United States Patent
Sharma

(10) Patent No.: US 10,413,436 B2
(45) Date of Patent: *Sep. 17, 2019

(54) INTRAGASTRIC DEVICE FOR TREATING OBESITY

(71) Applicant: SynerZ Medical, Inc., St. Louis, MO (US)

(72) Inventor: Virender K. Sharma, Paradise Valley, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/096,505

(22) Filed: Dec. 4, 2013

(65) Prior Publication Data

US 2014/0194917 A1 Jul. 10, 2014

Related U.S. Application Data

(63) Continuation of application No. 12/814,481, filed on Jun. 13, 2010, now Pat. No. 8,628,554.

(51) Int. Cl.
*A61F 5/00* (2006.01)
*A61F 2/04* (2013.01)
*A61F 2/915* (2013.01)

(52) U.S. Cl.
CPC .......... *A61F 5/0013* (2013.01); *A61F 5/0036* (2013.01); *A61F 5/0089* (2013.01);
(Continued)

(58) Field of Classification Search
CPC ................................................ A61F 2002/045
(Continued)

(56) References Cited

U.S. PATENT DOCUMENTS

| | | |
|---|---|---|
| 1,899,781 A | 2/1933 | Twiss |
| 2,464,933 A | 3/1949 | Kaslow |

(Continued)

FOREIGN PATENT DOCUMENTS

| | | |
|---|---|---|
| AU | 2010271294 A1 | 2/2012 |
| AU | 2011203951 A1 | 7/2012 |

(Continued)

OTHER PUBLICATIONS

US 8,668,662 B2, 03/2014, Levine (withdrawn)
(Continued)

*Primary Examiner* — Richard G Louis

(57) ABSTRACT

The present invention is directed toward an intragastric device used to treat obesity that includes a wire mesh structure capable of changing from a compressed pre-deployment shape to an expanded post-deployment shape with a greatly increased volume. The post-deployment shape contains a light weight at the top and a heavier weight at the bottom to ensure proper positioning within the stomach. In the post-deployment shape, the device contains larger spaces in the upper portion and smaller spaces in the lower portion to sequester food and delay gastric emptying. Alternatively, the device can be enveloped by a membrane containing larger holes at the top and smaller holes at the bottom to sequester food and delay gastric emptying. The device has a dynamic weight where the weight of the device in the pre-feeding stage is less than the weight of the device in feeding or post-feeding stage.

9 Claims, 26 Drawing Sheets

(52) U.S. Cl.
CPC . *A61F 2002/045* (2013.01); *A61F 2002/9155* (2013.01); *A61F 2220/0016* (2013.01); *A61F 2230/0071* (2013.01)

(58) Field of Classification Search
USPC .................................. 606/191; 623/23.65
See application file for complete search history.

(56) References Cited

U.S. PATENT DOCUMENTS

| | | |
|---|---|---|
| 3,780,740 A | 12/1973 | Rhea |
| 4,133,315 A | 1/1979 | Berman |
| 4,134,405 A | 1/1979 | Smit |
| 4,246,893 A | 1/1981 | Berson |
| 4,270,542 A | 6/1981 | Plumley |
| 4,279,251 A | 7/1981 | Rusch |
| 4,315,509 A | 2/1982 | Smit |
| 4,403,604 A | 9/1983 | Wilkinson |
| 4,416,267 A | 11/1983 | Garren |
| 4,441,215 A | 4/1984 | Kaster |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner |
| 4,723,547 A | 2/1988 | Kullas |
| 4,738,667 A | 4/1988 | Galloway |
| 4,763,653 A | 8/1988 | Rockey |
| 4,767,627 A | 8/1988 | Caldwell |
| 4,823,808 A | 4/1989 | Clegg |
| 4,846,836 A | 7/1989 | Reich |
| 4,878,905 A | 11/1989 | Blass |
| 4,899,747 A | 2/1990 | Garren |
| 4,913,141 A | 4/1990 | Hillstead |
| 5,035,706 A | 7/1991 | Gianturco |
| 5,037,387 A | 8/1991 | Quinn |
| 5,041,126 A | 8/1991 | Gianturco |
| 5,057,091 A | 10/1991 | Andersen |
| 5,104,399 A | 4/1992 | Lazarus |
| 5,152,756 A | 10/1992 | Quinn |
| 5,163,952 A | 11/1992 | Froix |
| 5,188,104 A | 2/1993 | Wernicke |
| 5,211,658 A | 5/1993 | Clouse |
| 5,234,454 A | 8/1993 | Bangs |
| 5,236,423 A | 8/1993 | Mix |
| 5,246,456 A | 9/1993 | Wilkinson |
| 5,259,399 A | 11/1993 | Brown |
| 5,279,553 A | 1/1994 | Winkler |
| 5,282,824 A | 2/1994 | Gianturco |
| 5,290,217 A | 3/1994 | Campos |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,327,914 A | 7/1994 | Shlain |
| 5,345,949 A | 9/1994 | Shlain |
| 5,364,353 A | 11/1994 | Corfitsen |
| 5,387,235 A | 2/1995 | Chuter |
| 5,401,241 A | 3/1995 | Delany |
| 5,405,377 A | 4/1995 | Cragg |
| 5,405,378 A | 4/1995 | Strecker |
| 5,423,872 A | 6/1995 | Cigaina |
| 5,443,498 A | 8/1995 | Fontaine |
| 5,456,713 A | 10/1995 | Chuter |
| 5,480,423 A | 1/1996 | Ravenscroft |
| 5,507,767 A | 4/1996 | Maeda |
| 5,507,771 A | 4/1996 | Gianturco |
| 5,514,176 A | 5/1996 | Bosley, Jr. |
| 5,536,274 A | 7/1996 | Neuss |
| 5,562,697 A | 10/1996 | Christiansen |
| 5,569,219 A | 10/1996 | Hakki |
| 5,593,434 A | 1/1997 | Williams |
| 5,611,787 A | 3/1997 | Demeter |
| 5,624,430 A | 4/1997 | Eton |
| 5,630,797 A | 5/1997 | Diedrich |
| 5,637,699 A | 6/1997 | Dorn |
| 5,653,743 A | 8/1997 | Martin |
| 5,658,322 A | 8/1997 | Fleming |
| 5,662,713 A | 9/1997 | Andersen |
| 5,665,064 A | 9/1997 | Bodicky |
| 5,668,263 A | 9/1997 | Hoyer |
| 5,674,241 A | 10/1997 | Bley |
| 5,690,692 A | 11/1997 | Fleming |
| 5,693,084 A | 12/1997 | Chuter |
| 5,700,272 A | 12/1997 | Gordon |
| 5,709,657 A | 1/1998 | Zimmon |
| 5,713,910 A | 2/1998 | Gordon |
| 5,715,832 A | 2/1998 | Koblish |
| 5,720,776 A | 2/1998 | Chuter |
| 5,733,325 A | 3/1998 | Robinson |
| 5,741,277 A | 4/1998 | Gordon |
| 5,741,279 A | 4/1998 | Gordon |
| 5,749,918 A | 5/1998 | Hogendijk |
| 5,755,777 A | 5/1998 | Chuter |
| 5,771,903 A | 6/1998 | Jakobsson |
| 5,800,456 A | 9/1998 | Maeda |
| 5,800,526 A | 9/1998 | Anderson |
| 5,817,466 A | 10/1998 | Hoyer |
| 5,820,584 A | 10/1998 | Crabb |
| 5,830,229 A | 11/1998 | Konya |
| 5,835,897 A | 11/1998 | Dang |
| 5,843,164 A | 12/1998 | Frantzen |
| 5,861,036 A | 1/1999 | Godin |
| 5,868,141 A | 2/1999 | Ellias |
| 5,876,445 A | 3/1999 | Andersen |
| 5,887,594 A | 3/1999 | LoCicero, III |
| 5,891,845 A | 4/1999 | Myers |
| 5,922,019 A | 7/1999 | Hankh |
| 5,955,579 A | 9/1999 | Leonard |
| 5,965,396 A | 10/1999 | Pan |
| 5,993,483 A | 11/1999 | Gianotti |
| 6,027,508 A | 2/2000 | Ren |
| 6,048,351 A | 4/2000 | Gordon |
| 6,087,129 A | 7/2000 | Newgard |
| 6,099,552 A | 8/2000 | Adams |
| 6,102,922 A | 8/2000 | Jakobsson |
| 6,113,609 A | 9/2000 | Adams |
| 6,117,911 A | 9/2000 | Grainger |
| 6,132,471 A | 10/2000 | Johlin, Jr. |
| 6,146,416 A | 11/2000 | Andersen |
| 6,159,238 A | 12/2000 | Killion |
| 6,180,082 B1 | 1/2001 | Woltering |
| 6,183,461 B1 | 2/2001 | Matsuura |
| 6,184,254 B1 | 2/2001 | Bukoski |
| 6,200,336 B1 | 3/2001 | Pavcnik |
| 6,200,600 B1 | 3/2001 | Rashid |
| 6,241,738 B1 | 6/2001 | Dereume |
| 6,245,761 B1 | 6/2001 | Britton |
| 6,251,132 B1 | 6/2001 | Ravenscroft |
| 6,254,642 B1 | 7/2001 | Taylor |
| 6,258,120 B1 | 7/2001 | McKenzie |
| 6,264,700 B1 | 7/2001 | Kilcoyne |
| 6,302,891 B1 | 10/2001 | Nadal |
| 6,302,917 B1 | 10/2001 | Dua |
| 6,303,637 B1 | 10/2001 | Bao |
| 6,322,538 B1 | 11/2001 | Elbert |
| 6,331,190 B1 | 12/2001 | Shokoohi |
| 6,332,877 B1 | 12/2001 | Michels |
| 6,364,868 B1 | 4/2002 | Ikeguchi |
| 6,370,511 B1 | 4/2002 | Dang |
| 6,387,114 B2 | 5/2002 | Adams |
| 6,406,840 B1 | 6/2002 | Li |
| 6,410,587 B1 | 6/2002 | Grainger |
| 6,424,864 B1 | 7/2002 | Matsuura |
| 6,450,989 B2 | 9/2002 | Dubrul |
| 6,454,785 B2 | 9/2002 | DeHoyosGarza |
| 6,485,409 B1 | 11/2002 | Voloshin |
| 6,494,888 B1 | 12/2002 | Laufer |
| 6,503,264 B1 | 1/2003 | Birk |
| 6,508,833 B2 | 1/2003 | Pavcnik |
| 6,524,335 B1 | 2/2003 | Hartley |
| 6,524,336 B1 | 2/2003 | Papazolgou |

(56) References Cited

U.S. PATENT DOCUMENTS

| | | |
|---|---|---|
| 6,530,951 B1 | 3/2003 | Bates |
| 6,531,491 B1 | 3/2003 | Kania |
| 6,534,524 B1 | 3/2003 | Kania |
| 6,537,247 B2 | 3/2003 | Shannon |
| 6,540,789 B1 | 4/2003 | Silverman |
| 6,544,291 B2 | 4/2003 | Taylor |
| 6,547,801 B1 | 4/2003 | Dargent |
| 6,558,400 B2 | 5/2003 | Deem |
| 6,558,429 B2 | 5/2003 | Taylor |
| 6,565,597 B1 | 5/2003 | Fearnot |
| 6,571,127 B1 | 5/2003 | Ben-Haim |
| 6,572,627 B2 | 6/2003 | Gabbay |
| 6,572,629 B2 | 6/2003 | Kalloo |
| 6,575,896 B2 | 6/2003 | Silverman |
| 6,589,213 B2 | 7/2003 | Reydel |
| 6,589,275 B1 | 7/2003 | Ivancev |
| 6,596,023 B1 | 7/2003 | Nunez |
| 6,623,518 B2 | 9/2003 | Thompson |
| 6,630,123 B1 | 10/2003 | Woltering |
| 6,635,079 B2 | 10/2003 | Unsworth |
| 6,656,194 B1 | 12/2003 | Gannoe |
| 6,663,639 B1 | 12/2003 | Laufer |
| 6,666,848 B2 | 12/2003 | Stone |
| 6,675,809 B2 | 1/2004 | Stack |
| 6,676,692 B2 | 1/2004 | Rabkin |
| 6,685,962 B2 | 2/2004 | Friedman |
| 6,695,875 B2 | 2/2004 | Stelter |
| 6,696,575 B2 | 2/2004 | Schmidt |
| 6,699,263 B2 | 3/2004 | Cope |
| 6,733,512 B2 | 5/2004 | McGhan |
| 6,734,208 B2 | 5/2004 | Grainger |
| 6,740,121 B2 | 5/2004 | Geitz |
| 6,743,198 B1 | 6/2004 | Tihon |
| 6,755,869 B2 | 6/2004 | Geitz |
| 6,761,733 B2 | 7/2004 | Chobotov |
| 6,764,518 B2 | 7/2004 | Godin |
| 6,773,440 B2 | 8/2004 | Gannoe |
| 6,773,441 B1 | 8/2004 | Laufer |
| 6,776,791 B1 | 8/2004 | Stallings |
| 6,776,999 B1 | 8/2004 | Krumme |
| 6,802,846 B2 | 10/2004 | Hauschild |
| 6,802,868 B2 | 10/2004 | Silverman |
| 6,844,349 B2 | 1/2005 | Kath |
| 6,845,776 B2 | 1/2005 | Stack |
| 6,855,153 B2 | 2/2005 | Saadat |
| 6,884,890 B2 | 4/2005 | Kania |
| 6,890,924 B2 | 5/2005 | Kath |
| 6,891,044 B2 | 5/2005 | Kania |
| 6,911,198 B2 | 6/2005 | Shachar |
| 6,932,838 B2 | 8/2005 | Schwartz |
| 6,939,370 B2 | 9/2005 | Hartley |
| 6,947,792 B2 | 9/2005 | Ben-Haim |
| 6,950,707 B2 | 9/2005 | Whitehurst |
| 6,994,095 B2 | 2/2006 | Burnett |
| 7,019,147 B1 | 3/2006 | Barth |
| 7,025,791 B2 | 4/2006 | Levine |
| 7,033,373 B2 | 4/2006 | delaTorre |
| 7,033,384 B2 | 4/2006 | Gannoe |
| 7,037,344 B2 | 5/2006 | Kagan |
| 7,041,120 B2 | 5/2006 | Li |
| 7,044,979 B2 | 5/2006 | Silverman |
| 7,056,305 B2 | 6/2006 | GarzaAlvarez |
| 7,060,080 B2 | 6/2006 | Bachmann |
| 7,063,860 B2 | 6/2006 | Chancellor |
| 7,066,945 B2 | 6/2006 | Hashiba |
| 7,071,337 B2 | 7/2006 | Kath |
| 7,083,629 B2 | 8/2006 | Weller |
| 7,084,171 B2 | 8/2006 | Grainger |
| 7,090,699 B2 | 8/2006 | Geitz |
| 7,097,665 B2 | 8/2006 | Stack |
| 7,111,627 B2 | 9/2006 | Stack |
| 7,120,497 B2 | 10/2006 | Ben-Haim |
| 7,121,283 B2 | 10/2006 | Stack |
| 7,122,058 B2 | 10/2006 | Levine |
| 7,128,750 B1 | 10/2006 | Stergiopulos |
| 7,141,581 B2 | 11/2006 | Bender |
| 7,141,587 B2 | 11/2006 | Kania |
| 7,145,008 B2 | 12/2006 | Kath |
| 7,146,984 B2 | 12/2006 | Stack |
| 7,148,380 B2 | 12/2006 | Wang |
| 7,152,607 B2 | 12/2006 | Stack |
| 7,153,314 B2 | 12/2006 | Laufer |
| 7,172,613 B2 | 2/2007 | Wazne |
| 7,189,750 B2 | 3/2007 | Assaf |
| 7,196,093 B2 | 3/2007 | Yuan |
| 7,208,499 B2 | 4/2007 | Kath |
| 7,211,114 B2 | 5/2007 | Bessler |
| 7,220,284 B2 | 5/2007 | Kagan |
| 7,221,978 B2 | 5/2007 | Ben-Haim |
| 7,230,098 B2 | 6/2007 | Cui |
| 7,235,562 B2 | 6/2007 | Kath |
| 7,238,191 B2 | 7/2007 | Bachmann |
| 7,267,694 B2 | 9/2007 | Levine |
| 7,271,262 B2 | 9/2007 | LaGreca |
| 7,273,451 B2 | 9/2007 | Sekine |
| 7,288,099 B2 | 10/2007 | Deem |
| 7,288,101 B2 | 10/2007 | Deem |
| 7,306,614 B2 | 12/2007 | Weller |
| 7,309,858 B2 | 12/2007 | Pappin |
| 7,314,443 B2 | 1/2008 | Jordan |
| 7,316,716 B2 | 1/2008 | Egan |
| 7,320,696 B2 | 1/2008 | Gazi |
| 7,329,285 B2 | 2/2008 | Levine |
| 7,330,747 B2 | 2/2008 | Maier |
| 7,330,753 B2 | 2/2008 | Policker |
| 7,332,493 B2 | 2/2008 | Kath |
| 7,332,513 B2 | 2/2008 | Assaf |
| 7,335,210 B2 | 2/2008 | Smit |
| 7,335,646 B2 | 2/2008 | Kieffer |
| 7,338,433 B2 | 3/2008 | Coe |
| 7,347,868 B2 | 3/2008 | Burnett |
| 7,347,875 B2 | 3/2008 | Levine |
| 7,354,454 B2 | 4/2008 | Stack |
| 7,364,591 B2 | 4/2008 | Silverman |
| 7,368,577 B2 | 5/2008 | Assaf |
| 7,371,862 B2 | 5/2008 | Vanotti |
| 7,410,988 B2 | 8/2008 | Dickson, Jr. |
| 7,416,885 B2 | 8/2008 | Freeman |
| 7,427,415 B2 | 9/2008 | Scharp |
| 7,435,739 B2 | 10/2008 | Chen |
| 7,462,487 B2 | 12/2008 | Tsao |
| 7,468,355 B2 | 12/2008 | Hamdi |
| 7,476,256 B2 | 1/2009 | Meade |
| 7,483,746 B2 | 1/2009 | Lee |
| 7,498,445 B2 | 3/2009 | Assaf |
| 7,503,922 B2 | 3/2009 | Deem |
| 7,510,559 B2 | 3/2009 | Deem |
| 7,511,070 B2 | 3/2009 | Grainger |
| 7,513,914 B2 | 4/2009 | Schurr |
| 7,530,985 B2 | 5/2009 | Takemoto |
| 7,547,312 B2 | 6/2009 | Bauman |
| 7,579,477 B2 | 8/2009 | Assaf |
| 7,582,313 B2 | 9/2009 | Faustman |
| 7,585,869 B2 | 9/2009 | Bhattacharya |
| 7,594,926 B2 | 9/2009 | Linder |
| 7,601,525 B2 | 10/2009 | Batich |
| 7,604,649 B2 | 10/2009 | McGuckin, Jr. |
| 7,608,114 B2 | 10/2009 | Levine |
| 7,620,454 B2 | 11/2009 | Dinsmoor |
| 7,620,560 B2 | 11/2009 | Dang |
| 7,625,939 B2 | 12/2009 | Heiser |
| 7,628,821 B2 | 12/2009 | Stack |
| 7,628,988 B2 | 12/2009 | Faustman |
| 7,637,905 B2 | 12/2009 | Saadat |
| 7,637,919 B2 | 12/2009 | Ishikawa |
| 7,654,951 B2 | 2/2010 | Ishikawa |
| 7,662,929 B2 | 2/2010 | Brown |
| 7,674,396 B2 | 3/2010 | Sterling |
| 7,674,457 B2 | 3/2010 | Borlongan |
| 7,678,068 B2 | 3/2010 | Levine |
| 7,682,330 B2 | 3/2010 | Meade |
| 7,691,152 B2 | 4/2010 | Silverman |
| 7,695,446 B2 | 4/2010 | Levine |
| 7,696,213 B2 | 4/2010 | Cheng |

(56) References Cited

U.S. PATENT DOCUMENTS

| | | |
|---|---|---|
| 7,699,863 B2 | 4/2010 | Marco |
| 7,725,333 B2 | 5/2010 | Dang |
| 7,727,143 B2 | 6/2010 | Birk |
| 7,731,757 B2 | 6/2010 | Taylor |
| 7,736,373 B2 | 6/2010 | Laufer |
| 7,741,336 B2 | 6/2010 | Kath |
| 7,742,818 B2 | 6/2010 | Dinsmoor |
| 7,749,254 B2 | 7/2010 | Sobelman |
| 7,758,535 B2 | 7/2010 | Levine |
| 7,765,008 B2 | 7/2010 | Ben-Haim |
| 7,766,861 B2 | 8/2010 | Levine |
| 7,766,973 B2 | 8/2010 | Levine |
| 7,771,382 B2 | 8/2010 | Levine |
| 7,774,216 B2 | 8/2010 | Dang |
| 7,780,590 B2 | 8/2010 | Birk |
| 7,794,447 B2 | 9/2010 | Dann |
| 7,795,290 B2 | 9/2010 | Dickson, Jr. |
| 7,798,954 B2 | 9/2010 | Birk |
| 7,799,088 B2 | 9/2010 | Geitz |
| 7,803,177 B2 | 9/2010 | Hartley |
| 7,803,195 B2 | 9/2010 | Levy |
| 7,811,298 B2 | 10/2010 | Birk |
| 7,811,299 B2 | 10/2010 | Bachmann |
| 7,815,589 B2 | 10/2010 | Meade |
| 7,815,591 B2 | 10/2010 | Levine |
| 7,819,836 B2 | 10/2010 | Levine |
| 7,833,280 B2 | 11/2010 | Stack |
| 7,837,643 B2 | 11/2010 | Levine |
| 7,837,669 B2 | 11/2010 | Dann |
| 7,838,524 B2 | 11/2010 | Lee |
| 7,840,269 B2 | 11/2010 | Policker |
| 7,846,138 B2 | 12/2010 | Dann |
| 7,850,704 B2 | 12/2010 | Burnett |
| 7,862,574 B2 | 1/2011 | Deem |
| 7,867,283 B2 | 1/2011 | Krueger |
| 7,881,797 B2 | 2/2011 | Griffin |
| 7,883,524 B2 | 2/2011 | Chen |
| 7,892,214 B2 | 2/2011 | Kagan |
| 7,892,827 B2 | 2/2011 | Matschiner |
| 7,901,419 B2 | 3/2011 | Bachmann |
| 7,909,838 B2 | 3/2011 | Deem |
| 7,922,684 B2 | 4/2011 | Weitzner |
| 7,928,109 B2 | 4/2011 | Luzzio |
| 7,935,073 B2 | 5/2011 | Levine |
| 7,945,323 B2 | 5/2011 | Jaax |
| 7,959,552 B2 | 6/2011 | Jordan |
| 7,959,640 B2 | 6/2011 | Kantsevoy |
| 7,960,345 B2 | 6/2011 | Kim |
| 7,966,071 B2 | 6/2011 | Ben-Haim |
| 7,968,575 B2 | 6/2011 | Assaf |
| 7,972,346 B2 | 7/2011 | Bachmann |
| 7,976,488 B2 | 7/2011 | Levine |
| 7,979,290 B2 | 7/2011 | Dang |
| 7,981,162 B2 | 7/2011 | Stack |
| 7,981,163 B2 | 7/2011 | Meade |
| 7,985,844 B2 | 7/2011 | Brown |
| 7,998,220 B2 | 8/2011 | Murphy |
| 7,998,966 B2 | 8/2011 | Bearss |
| 8,002,731 B2 | 8/2011 | Weitzner |
| 8,003,806 B2 | 8/2011 | Bloxham |
| 8,006,701 B2 | 8/2011 | Bilotti |
| 8,007,507 B2 | 8/2011 | Waller |
| 8,008,449 B2 | 8/2011 | Korman |
| 8,012,135 B2 | 9/2011 | Dann |
| 8,012,140 B1 | 9/2011 | Kagan |
| 8,012,162 B2 | 9/2011 | Bachmann |
| 8,012,966 B2 | 9/2011 | Tang |
| 8,021,693 B2 | 9/2011 | Faustman |
| 8,043,206 B2 | 10/2011 | Birk |
| 8,043,248 B2 | 10/2011 | Pasricha |
| 8,048,169 B2 | 11/2011 | Burnett |
| 8,048,170 B2 | 11/2011 | Silverman |
| 8,057,420 B2 | 11/2011 | Meade |
| 8,057,494 B2 | 11/2011 | Laufer |
| 8,062,656 B2 | 11/2011 | Oh-Lee |
| 8,066,689 B2 | 11/2011 | Mitelberg |
| 8,070,743 B2 | 12/2011 | Kagan |
| 8,070,824 B2 | 12/2011 | Burnett |
| 8,075,577 B2 | 12/2011 | Deem |
| 8,079,974 B2 | 12/2011 | Stergiopulos |
| 8,080,022 B2 | 12/2011 | Deem |
| 8,080,025 B2 | 12/2011 | Deem |
| 8,084,457 B2 | 12/2011 | Choidas |
| 8,084,484 B2 | 12/2011 | Frank |
| 8,092,482 B2 | 1/2012 | Gannoe |
| 8,095,219 B2 | 1/2012 | Lee |
| 8,096,966 B2 | 1/2012 | Levine |
| 8,105,392 B2 | 1/2012 | Durgin |
| 8,106,197 B2 | 1/2012 | Cui |
| 8,109,895 B2 | 2/2012 | Williams |
| 8,114,045 B2 | 2/2012 | Surti |
| 8,114,893 B2 | 2/2012 | Baell |
| 8,116,883 B2 | 2/2012 | Williams |
| 8,118,774 B2 | 2/2012 | Dann |
| 8,121,869 B2 | 2/2012 | Dang |
| 8,123,765 B2 | 2/2012 | Deem |
| 8,123,766 B2 | 2/2012 | Bauman |
| 8,123,767 B2 | 2/2012 | Bauman |
| 8,134,010 B2 | 3/2012 | Assaf |
| 8,137,301 B2 | 3/2012 | Levine |
| 8,137,662 B2 | 3/2012 | Freeman |
| 8,142,469 B2 | 3/2012 | Sosnowski |
| 8,142,514 B2 | 3/2012 | Geitz |
| 8,147,561 B2 | 4/2012 | Binmoeller |
| 8,162,871 B2 | 4/2012 | Levine |
| 8,173,129 B2 | 5/2012 | Faustman |
| 8,177,853 B2 | 5/2012 | Stack |
| 8,182,441 B2 | 5/2012 | Swain |
| 8,182,459 B2 | 5/2012 | Dann |
| 8,182,543 B2 | 5/2012 | Schurr |
| 8,187,289 B2 | 5/2012 | Tacchino |
| 8,207,166 B2 | 6/2012 | Lee |
| 8,211,186 B2 | 7/2012 | Belhe |
| 8,216,266 B2 | 7/2012 | Hively |
| 8,216,268 B2 | 7/2012 | Haller |
| 8,219,201 B2 | 7/2012 | Ben-Haim |
| 8,226,593 B2 | 7/2012 | Graham |
| 8,226,602 B2 | 7/2012 | Quijana |
| 8,232,273 B2 | 7/2012 | Baell |
| 8,236,023 B2 | 8/2012 | Birk |
| 8,247,411 B2 | 8/2012 | Luzzio |
| 8,252,816 B2 | 8/2012 | Frank |
| 8,268,821 B2 | 9/2012 | Nadeson |
| 8,273,755 B2 | 9/2012 | Cheng |
| 8,277,468 B2 | 10/2012 | Laufer |
| 8,282,598 B2 | 10/2012 | Belhe |
| 8,282,666 B2 | 10/2012 | Birk |
| 8,290,582 B2 | 10/2012 | Lin |
| 8,292,800 B2 | 10/2012 | Stone |
| 8,296,165 B2 | 10/2012 | Dang |
| 8,299,022 B2 | 10/2012 | Dong |
| 8,303,669 B2 | 11/2012 | Meade |
| 8,308,630 B2 | 11/2012 | Birk |
| 8,308,813 B2 | 11/2012 | Krueger |
| 8,317,677 B2 | 11/2012 | Bertolote |
| 8,323,180 B2 | 12/2012 | Birk |
| 8,323,229 B2 | 12/2012 | Shin |
| 8,334,263 B2 | 12/2012 | Nadeson |
| 8,337,567 B2 | 12/2012 | Stack |
| 8,337,829 B2 | 12/2012 | Freeman |
| 8,357,501 B2 | 1/2013 | Jackson |
| 8,362,251 B2 | 1/2013 | Tang |
| 8,366,602 B2 | 2/2013 | Birk |
| 8,376,929 B2 | 2/2013 | Birk |
| 8,377,081 B2 | 2/2013 | Bachmann |
| 8,382,780 B2 | 2/2013 | Birk |
| 8,398,654 B2 | 3/2013 | Franklin |
| 8,399,223 B2 | 3/2013 | Park |
| 8,403,877 B2 | 3/2013 | Priplata |
| 8,409,221 B2 | 4/2013 | Franklin |
| 8,409,226 B2 | 4/2013 | Kantsevoy |
| 8,414,559 B2 | 4/2013 | Gross |
| 8,425,451 B2 | 4/2013 | Levine |
| 8,430,894 B2 | 4/2013 | Brooks |

(56) References Cited

U.S. PATENT DOCUMENTS

| | | | |
|---|---|---|---|
| 8,430,895 | B2 | 4/2013 | Brooks |
| 8,431,597 | B2 | 4/2013 | Munchhof |
| 8,436,011 | B2 | 5/2013 | Bellevergue |
| 8,440,822 | B2 | 5/2013 | Luzzio |
| 8,465,447 | B2 | 6/2013 | Krueger |
| 8,470,815 | B2 | 6/2013 | SaulnierSholler |
| 8,475,401 | B2 | 7/2013 | Priplata |
| 8,486,153 | B2 | 7/2013 | Levine |
| 8,491,472 | B2 | 7/2013 | Mitelberg |
| 8,491,519 | B2 | 7/2013 | Chin |
| 8,496,931 | B2 | 7/2013 | Pogue |
| 8,506,517 | B2 | 8/2013 | Stergiopulos |
| 8,506,532 | B2 | 8/2013 | Olroyd |
| 8,507,274 | B2 | 8/2013 | Melton |
| 8,515,542 | B2 | 8/2013 | Jaax |
| 8,517,915 | B2 | 8/2013 | Perron |
| 8,518,970 | B2 | 8/2013 | Baell |
| 8,529,943 | B2 | 9/2013 | Kliger |
| 8,556,918 | B2 | 10/2013 | Bauman |
| 8,556,925 | B2 | 10/2013 | Makower |
| 8,556,934 | B2 | 10/2013 | Godin |
| 8,568,488 | B2 | 10/2013 | Stack |
| 8,579,988 | B2 | 11/2013 | Burnett |
| 8,585,628 | B2 | 11/2013 | Harris |
| 8,585,753 | B2 | 11/2013 | Scanlon |
| 8,585,771 | B2 | 11/2013 | Binmoeller |
| 8,591,452 | B2 | 11/2013 | Priplata |
| 8,591,533 | B2 | 11/2013 | Needleman |
| 8,591,598 | B2 | 11/2013 | Silverman |
| 8,597,224 | B2 | 12/2013 | Vargas |
| 8,603,186 | B2 | 12/2013 | Binmoeller |
| 8,613,749 | B2 | 12/2013 | Deem |
| 8,623,893 | B2 | 1/2014 | Lassalle |
| 8,628,554 | B2 | 1/2014 | Sharma |
| 8,628,583 | B2 | 1/2014 | Meade |
| 8,633,204 | B2 | 1/2014 | Cheng |
| 8,636,683 | B2 | 1/2014 | Chin |
| 8,636,751 | B2 | 1/2014 | Albrecht |
| 8,642,623 | B2 | 2/2014 | Frank |
| 8,652,083 | B2 | 2/2014 | Weitzner |
| 8,657,885 | B2 | 2/2014 | Burnett |
| 8,663,301 | B2 | 3/2014 | Riina |
| 8,663,338 | B2 | 3/2014 | Burnett |
| 8,678,993 | B2 | 3/2014 | Stroumpoulis |
| 8,679,137 | B2 | 3/2014 | Bauman |
| 8,683,881 | B2 | 4/2014 | Bouasaysy |
| 8,691,271 | B2 | 4/2014 | Burnett |
| 8,698,373 | B2 | 4/2014 | Augarten |
| 8,702,641 | B2 | 4/2014 | Belhe |
| 8,702,642 | B2 | 4/2014 | Belhe |
| 8,708,979 | B2 | 4/2014 | Honaryar |
| 8,715,158 | B2 | 5/2014 | Honaryar |
| 8,725,435 | B2 | 5/2014 | Snow |
| 8,753,369 | B2 | 6/2014 | Murature |
| 8,758,221 | B2 | 6/2014 | Snow |
| 8,764,624 | B2 | 7/2014 | Snow |
| 8,771,219 | B2 | 7/2014 | Meade |
| 8,795,301 | B2 | 8/2014 | Burnett |
| 8,801,597 | B2 | 8/2014 | Franklin |
| 8,801,647 | B2 | 8/2014 | Melanson |
| 8,808,270 | B2 | 8/2014 | Dann |
| 8,821,373 | B2 | 9/2014 | Schwab |
| 8,821,429 | B2 | 9/2014 | Vargas |
| 8,821,430 | B2 | 9/2014 | Stergiopulos |
| 8,821,521 | B2 | 9/2014 | Burnett |
| 8,821,584 | B2 | 9/2014 | Burnett |
| 8,834,405 | B2 | 9/2014 | Meade |
| 8,834,553 | B2 | 9/2014 | Melanson |
| 8,840,541 | B2 | 9/2014 | Snow |
| 8,840,679 | B2 | 9/2014 | Durgin |
| 8,840,952 | B2 | 9/2014 | Ashby |
| 8,845,513 | B2 | 9/2014 | Coe |
| 8,845,672 | B2 | 9/2014 | Alverdy |
| 8,858,421 | B2 | 10/2014 | Honaryar |
| 8,864,840 | B2 | 10/2014 | Dominguez |
| 8,870,806 | B2 | 10/2014 | Levine |
| 8,870,966 | B2 | 10/2014 | Schwab |
| 8,876,694 | B2 | 11/2014 | Honaryar |
| 8,882,655 | B2 | 11/2014 | Nitka |
| 8,882,698 | B2 | 11/2014 | Levine |
| 8,882,728 | B2 | 11/2014 | Harders |
| 8,882,798 | B2 | 11/2014 | Schwab |
| 8,888,732 | B2 | 11/2014 | Raven |
| 8,888,797 | B2 | 11/2014 | Burnett |
| 8,894,568 | B2 | 11/2014 | Kwok |
| 8,900,117 | B2 | 12/2014 | Birk |
| 8,900,118 | B2 | 12/2014 | Birk |
| 8,905,915 | B2 | 12/2014 | Birk |
| 8,905,916 | B2 | 12/2014 | Jacobs |
| 8,920,358 | B2 | 12/2014 | Levine |
| 8,920,447 | B2 | 12/2014 | Dominguez |
| 8,932,247 | B2 | 1/2015 | Stergiopulos |
| 8,939,888 | B2 | 1/2015 | Augarten |
| 8,956,318 | B2 | 2/2015 | Miller |
| 8,956,380 | B2 | 2/2015 | Dominguez |
| 8,961,393 | B2 | 2/2015 | Rion |
| 8,961,394 | B2 | 2/2015 | Honaryar |
| 8,968,177 | B2 | 3/2015 | Silverman |
| 8,968,270 | B2 | 3/2015 | Kagan |
| 8,979,735 | B2 | 3/2015 | Augarten |
| 8,992,415 | B2 | 3/2015 | Deuel |
| 8,992,559 | B2 | 3/2015 | Weitzner |
| 9,017,358 | B2 | 4/2015 | Schwab |
| 9,023,062 | B2 | 5/2015 | Franklin |
| 9,023,063 | B2 | 5/2015 | Franklin |
| 9,028,394 | B2 | 5/2015 | Honaryar |
| 9,039,649 | B2 | 5/2015 | Neisz |
| 9,044,298 | B2 | 6/2015 | Franklin |
| 9,044,300 | B2 | 6/2015 | Belhe |
| 9,050,165 | B2 | 6/2015 | Perron |
| 9,050,168 | B2 | 6/2015 | Neisz |
| 9,050,174 | B2 | 6/2015 | Pecor |
| 9,060,844 | B2 | 6/2015 | Kagan |
| 9,066,780 | B2 | 6/2015 | Weber |
| 9,072,579 | B2 | 7/2015 | Birk |
| 9,084,669 | B2 | 7/2015 | Meade |
| 9,089,395 | B2 | 7/2015 | Honaryar |
| 9,095,405 | B2 | 8/2015 | Babkes |
| 9,095,416 | B2 | 8/2015 | Meade |
| 2001/0011543 | A1 | 8/2001 | Forsell |
| 2002/0006962 | A1 | 1/2002 | Wang |
| 2002/0071857 | A1 | 6/2002 | Kararli |
| 2002/0091439 | A1 | 7/2002 | Baker |
| 2002/0137086 | A1 | 9/2002 | Olek |
| 2002/0143387 | A1 | 10/2002 | Soetikno |
| 2002/0155100 | A1 | 10/2002 | Kieffer |
| 2002/0165572 | A1 | 11/2002 | Saadat |
| 2002/0165738 | A1 | 11/2002 | Dang |
| 2002/0169165 | A1 | 11/2002 | Kath |
| 2002/0173987 | A1 | 11/2002 | Dang |
| 2002/0173988 | A1 | 11/2002 | Dang |
| 2002/0173989 | A1 | 11/2002 | Dang |
| 2002/0173992 | A1 | 11/2002 | Dang |
| 2002/0183768 | A1 | 12/2002 | Deem |
| 2002/0193816 | A1 | 12/2002 | Laufer |
| 2002/0193828 | A1 | 12/2002 | Griffin |
| 2002/0197656 | A1 | 12/2002 | Li |
| 2003/0018299 | A1 | 1/2003 | Stone |
| 2003/0040804 | A1 | 2/2003 | Stack |
| 2003/0040808 | A1 | 2/2003 | Stack |
| 2003/0050684 | A1 | 3/2003 | Abrams |
| 2003/0053985 | A1 | 3/2003 | Shachar |
| 2003/0055465 | A1 | 3/2003 | Ben-Haim |
| 2003/0055466 | A1 | 3/2003 | Ben-Haim |
| 2003/0055467 | A1 | 3/2003 | Ben-Haim |
| 2003/0064970 | A1 | 4/2003 | Grainger |
| 2003/0065359 | A1 | 4/2003 | Weller |
| 2003/0066987 | A1 | 4/2003 | Schmidt |
| 2003/0086975 | A1 | 5/2003 | Ringeisen |
| 2003/0108597 | A1 | 6/2003 | Chancellor |
| 2003/0109892 | A1 | 6/2003 | Deem |
| 2003/0109935 | A1* | 6/2003 | Geitz ............ 623/23.65 |
| 2003/0120265 | A1 | 6/2003 | Deem |
| 2003/0153905 | A1 | 8/2003 | Edwards |

(56) References Cited

U.S. PATENT DOCUMENTS

| | | |
|---|---|---|
| 2003/0158217 A1 | 8/2003 | Kath |
| 2003/0171261 A1 | 9/2003 | Livingston |
| 2003/0171386 A1 | 9/2003 | Connell |
| 2003/0190368 A1 | 10/2003 | Stoughton |
| 2003/0191476 A1 | 10/2003 | Smit |
| 2003/0191492 A1 | 10/2003 | Gellman |
| 2003/0199989 A1 | 10/2003 | Stack |
| 2003/0199990 A1 | 10/2003 | Stack |
| 2003/0199991 A1 | 10/2003 | Stack |
| 2003/0208260 A1 | 11/2003 | Lau |
| 2003/0232752 A1 | 12/2003 | Freeman |
| 2004/0024386 A1 | 2/2004 | Deem |
| 2004/0028658 A1 | 2/2004 | Faustman |
| 2004/0039452 A1* | 2/2004 | Bessler ............... A61F 2/07 623/23.65 |
| 2004/0045045 A1 | 3/2004 | Mather |
| 2004/0062778 A1 | 4/2004 | Shefer |
| 2004/0073278 A1 | 4/2004 | Pachys |
| 2004/0087876 A1 | 5/2004 | Eskuri |
| 2004/0092892 A1 | 5/2004 | Kagan |
| 2004/0097428 A1 | 5/2004 | Hamdi |
| 2004/0106892 A1 | 6/2004 | Stone |
| 2004/0107004 A1* | 6/2004 | Levine ............ A61B 17/0401 623/23.64 |
| 2004/0117031 A1* | 6/2004 | Stack et al. ............ 623/23.65 |
| 2004/0122452 A1 | 6/2004 | Deem |
| 2004/0122453 A1 | 6/2004 | Deem |
| 2004/0122456 A1 | 6/2004 | Saadat |
| 2004/0127800 A1 | 7/2004 | Kimball |
| 2004/0133147 A1 | 7/2004 | Woo |
| 2004/0138529 A1 | 7/2004 | Wiltshire |
| 2004/0138760 A1 | 7/2004 | Schurr |
| 2004/0143342 A1 | 7/2004 | Stack |
| 2004/0147816 A1 | 7/2004 | Policker |
| 2004/0158331 A1 | 8/2004 | Stack |
| 2004/0170631 A1 | 9/2004 | Yacoby-Zeevi |
| 2004/0171634 A1 | 9/2004 | Kania |
| 2004/0180086 A1 | 9/2004 | Ramtoola |
| 2004/0181242 A1 | 9/2004 | Stack |
| 2004/0192598 A1 | 9/2004 | Kragie |
| 2004/0193184 A1 | 9/2004 | Laufer |
| 2004/0204429 A1 | 10/2004 | Yuan |
| 2004/0220177 A1 | 11/2004 | Kath |
| 2004/0220248 A1 | 11/2004 | Kania |
| 2004/0220682 A1 | 11/2004 | Levine |
| 2004/0225191 A1 | 11/2004 | Sekine |
| 2004/0236381 A1 | 11/2004 | Dinsmoor |
| 2004/0236382 A1 | 11/2004 | Dinsmoor |
| 2004/0242604 A1 | 12/2004 | Bhattacharya |
| 2004/0243152 A1 | 12/2004 | Taylor |
| 2004/0254204 A1 | 12/2004 | Kath |
| 2005/0004430 A1 | 1/2005 | Lee |
| 2005/0004681 A1* | 1/2005 | Stack .................. A61F 2/04 623/23.65 |
| 2005/0009840 A1 | 1/2005 | Cui |
| 2005/0020667 A1 | 1/2005 | Grainger |
| 2005/0037999 A1 | 2/2005 | LaGreca |
| 2005/0038097 A1 | 2/2005 | Bender |
| 2005/0055039 A1 | 3/2005 | Burnett |
| 2005/0075354 A1 | 4/2005 | Li |
| 2005/0085923 A1 | 4/2005 | Levine |
| 2005/0089577 A1* | 4/2005 | Yokoyama et al. .......... 424/488 |
| 2005/0101011 A1 | 5/2005 | Tsao |
| 2005/0101618 A1 | 5/2005 | Connell |
| 2005/0124599 A1 | 6/2005 | Kath |
| 2005/0124662 A1 | 6/2005 | Kania |
| 2005/0125020 A1 | 6/2005 | Meade |
| 2005/0125075 A1 | 6/2005 | Meade |
| 2005/0130994 A1 | 6/2005 | Chen |
| 2005/0143765 A1 | 6/2005 | Bachmann |
| 2005/0143766 A1 | 6/2005 | Bachmann |
| 2005/0158288 A1 | 7/2005 | Faustman |
| 2005/0159435 A1 | 7/2005 | Kath |
| 2005/0159769 A1 | 7/2005 | Alverdy |
| 2005/0164388 A1 | 7/2005 | Son |
| 2005/0169902 A1 | 8/2005 | Borlongan |
| 2005/0171556 A1 | 8/2005 | Murphy |
| 2005/0196423 A1 | 9/2005 | Batich |
| 2005/0197714 A1 | 9/2005 | Sayet |
| 2005/0251182 A1 | 11/2005 | Bachmann |
| 2005/0256111 A1 | 11/2005 | Kath |
| 2005/0256125 A1 | 11/2005 | Kath |
| 2005/0256144 A1 | 11/2005 | Kath |
| 2005/0256587 A1 | 11/2005 | Egan |
| 2005/0267595 A1 | 12/2005 | Chen |
| 2005/0273060 A1 | 12/2005 | Levy |
| 2006/0002899 A1 | 1/2006 | Rice |
| 2006/0009858 A1 | 1/2006 | Levine |
| 2006/0015125 A1* | 1/2006 | Swain ...................... 606/151 |
| 2006/0015151 A1 | 1/2006 | Aldrich |
| 2006/0020278 A1 | 1/2006 | Burnett |
| 2006/0025799 A1 | 2/2006 | Basu |
| 2006/0052416 A1 | 3/2006 | Dickson |
| 2006/0064120 A1* | 3/2006 | Levine ............... A61F 2/04 606/153 |
| 2006/0069138 A1 | 3/2006 | Assaf |
| 2006/0069139 A1 | 3/2006 | Assaf |
| 2006/0069400 A1 | 3/2006 | Burnett |
| 2006/0074073 A1 | 4/2006 | Steinfeldt |
| 2006/0078993 A1 | 4/2006 | Phan |
| 2006/0084696 A1 | 4/2006 | Grainger |
| 2006/0089627 A1 | 4/2006 | Burnett |
| 2006/0105454 A1 | 5/2006 | Son |
| 2006/0116383 A1 | 6/2006 | Bloxham |
| 2006/0127437 A1 | 6/2006 | Kennedy |
| 2006/0134109 A1 | 6/2006 | Gaitanaris |
| 2006/0134186 A1 | 6/2006 | Carlton |
| 2006/0142731 A1 | 6/2006 | Brooks |
| 2006/0142787 A1 | 6/2006 | Weller |
| 2006/0183718 A1 | 8/2006 | Assaf |
| 2006/0183912 A1 | 8/2006 | Assaf |
| 2006/0183913 A1 | 8/2006 | Assaf |
| 2006/0228775 A1 | 10/2006 | Collier |
| 2006/0241130 A1 | 10/2006 | Keinan |
| 2006/0241748 A1 | 10/2006 | Lee |
| 2006/0271088 A1 | 11/2006 | Alfrhan |
| 2006/0276713 A1 | 12/2006 | Maier |
| 2007/0003610 A1 | 1/2007 | Chancellor |
| 2007/0021382 A1 | 1/2007 | Assaf |
| 2007/0021988 A1 | 1/2007 | Dang |
| 2007/0027548 A1 | 2/2007 | Levine |
| 2007/0032879 A1 | 2/2007 | Levine |
| 2007/0037883 A1 | 2/2007 | Dusting |
| 2007/0060940 A1 | 3/2007 | Brazzini |
| 2007/0072874 A1 | 3/2007 | Cui |
| 2007/0072885 A1 | 3/2007 | Bhattacharya |
| 2007/0078435 A1 | 4/2007 | Stone |
| 2007/0083224 A1 | 4/2007 | Hively |
| 2007/0083271 A1 | 4/2007 | Levine |
| 2007/0088389 A1 | 4/2007 | Dunkin |
| 2007/0100367 A1 | 5/2007 | Quijano |
| 2007/0100368 A1 | 5/2007 | Quijano |
| 2007/0104754 A1 | 5/2007 | Sterling |
| 2007/0105861 A1 | 5/2007 | Lee |
| 2007/0112020 A1 | 5/2007 | Vanotti |
| 2007/0118158 A1 | 5/2007 | Deem |
| 2007/0118159 A1 | 5/2007 | Deem |
| 2007/0118168 A1 | 5/2007 | Lointier |
| 2007/0135335 A1 | 6/2007 | Collier |
| 2007/0135825 A1 | 6/2007 | Binmoeller |
| 2007/0135829 A1 | 6/2007 | Paganon |
| 2007/0135831 A1 | 6/2007 | Burnett |
| 2007/0148129 A1 | 6/2007 | Shortman |
| 2007/0149994 A1 | 6/2007 | Sosnowski |
| 2007/0156248 A1 | 7/2007 | Marco |
| 2007/0167963 A1 | 7/2007 | Deem |
| 2007/0173881 A1 | 7/2007 | Birk |
| 2007/0178160 A1 | 8/2007 | Burnett |
| 2007/0185176 A1 | 8/2007 | VanGelder |
| 2007/0185540 A1 | 8/2007 | Ben-Haim |
| 2007/0191344 A1 | 8/2007 | Choidas |
| 2007/0198039 A1 | 8/2007 | Jones |
| 2007/0198074 A1 | 8/2007 | Dann |
| 2007/0207186 A1 | 9/2007 | Scanlon |

(56) References Cited

U.S. PATENT DOCUMENTS

| | | |
|---|---|---|
| 2007/0210018 A1 | 9/2007 | Wallwiener |
| 2007/0213740 A1 | 9/2007 | Deem |
| 2007/0213748 A1 | 9/2007 | Deem |
| 2007/0219570 A1 | 9/2007 | Deem |
| 2007/0250083 A1 | 10/2007 | Deem |
| 2007/0250132 A1 | 10/2007 | Burnett |
| 2007/0255379 A1 | 11/2007 | Williams |
| 2007/0265598 A1 | 11/2007 | Karasik |
| 2007/0265709 A1 | 11/2007 | Rajan |
| 2007/0275902 A1 | 11/2007 | Gonda |
| 2007/0275962 A1 | 11/2007 | Koul |
| 2007/0276428 A1 | 11/2007 | Haller |
| 2007/0282349 A1 | 12/2007 | Deem |
| 2007/0282452 A1 | 12/2007 | Weitzner |
| 2007/0282453 A1 | 12/2007 | Weitzner |
| 2007/0286856 A1 | 12/2007 | Brown |
| 2007/0293885 A1 | 12/2007 | Binmoeller |
| 2007/0299320 A1 | 12/2007 | Policker |
| 2008/0021742 A1 | 1/2008 | Dang |
| 2008/0026072 A1* | 1/2008 | Nakayama et al. .......... 424/535 |
| 2008/0027469 A1 | 1/2008 | Bachmann |
| 2008/0039463 A1 | 2/2008 | Nadeson |
| 2008/0051849 A1 | 2/2008 | Ben-Haim |
| 2008/0058887 A1 | 3/2008 | Griffin |
| 2008/0058889 A1 | 3/2008 | Ben-Haim |
| 2008/0058891 A1 | 3/2008 | Ben-Haim |
| 2008/0059231 A1 | 3/2008 | Dang |
| 2008/0065136 A1 | 3/2008 | Young |
| 2008/0065421 A1 | 3/2008 | Dang |
| 2008/0071383 A1 | 3/2008 | Levine |
| 2008/0090801 A1 | 4/2008 | Cheng |
| 2008/0097466 A1 | 4/2008 | Levine |
| 2008/0097513 A1* | 4/2008 | Kaji ................ A61B 17/12099 606/192 |
| 2008/0097788 A1 | 4/2008 | Dang |
| 2008/0120734 A1 | 5/2008 | Kieffer |
| 2008/0154129 A1 | 6/2008 | Mizunuma |
| 2008/0161838 A1 | 7/2008 | DArcangelo |
| 2008/0175828 A1 | 7/2008 | Freeman |
| 2008/0187575 A1 | 8/2008 | Klebl |
| 2008/0194574 A1 | 8/2008 | Eikhoff |
| 2008/0194596 A1 | 8/2008 | Letrent |
| 2008/0195226 A1 | 8/2008 | Williams |
| 2008/0207677 A1 | 8/2008 | Muller |
| 2008/0208241 A1 | 8/2008 | Weiner |
| 2008/0208355 A1 | 8/2008 | Stack |
| 2008/0208356 A1 | 8/2008 | Stack |
| 2008/0208357 A1 | 8/2008 | Melanson |
| 2008/0214545 A1 | 9/2008 | Lee |
| 2008/0221595 A1 | 9/2008 | Surti |
| 2008/0228030 A1 | 9/2008 | Godin |
| 2008/0228066 A1 | 9/2008 | Waitzman |
| 2008/0233163 A1 | 9/2008 | Assaf |
| 2008/0234718 A1 | 9/2008 | Paganon |
| 2008/0234834 A1 | 9/2008 | Meade |
| 2008/0243071 A1 | 10/2008 | Quijano |
| 2008/0243166 A1 | 10/2008 | Paganon |
| 2008/0243167 A1 | 10/2008 | Paganon |
| 2008/0249533 A1 | 10/2008 | Godin |
| 2008/0249635 A1 | 10/2008 | Weitzner |
| 2008/0255594 A1 | 10/2008 | Cully |
| 2008/0255678 A1 | 10/2008 | Cully |
| 2008/0260797 A1 | 10/2008 | Oh-Lee |
| 2008/0261258 A1 | 10/2008 | Smith |
| 2008/0262529 A1 | 10/2008 | Jacques |
| 2008/0269289 A1 | 10/2008 | Frank |
| 2008/0269555 A1 | 10/2008 | Paganon |
| 2008/0281257 A1* | 11/2008 | Waller ............................ 604/28 |
| 2008/0281375 A1 | 11/2008 | Chen |
| 2008/0293618 A1 | 11/2008 | Heiser |
| 2008/0293733 A1 | 11/2008 | Bearss |
| 2008/0300234 A1 | 12/2008 | Kath |
| 2008/0302855 A1 | 12/2008 | Bilotti |
| 2009/0005867 A1 | 1/2009 | Lefranc |
| 2009/0012544 A1 | 1/2009 | Thompson |
| 2009/0042785 A1 | 2/2009 | Matschiner |
| 2009/0048313 A1 | 2/2009 | Dickson |
| 2009/0053182 A1 | 2/2009 | Ichim |
| 2009/0054395 A1 | 2/2009 | Luzzio |
| 2009/0062401 A1 | 3/2009 | Odermatt |
| 2009/0088676 A1 | 4/2009 | Murata |
| 2009/0093839 A1 | 4/2009 | Kelleher |
| 2009/0105562 A1 | 4/2009 | Chiou |
| 2009/0111805 A1 | 4/2009 | Morris |
| 2009/0138094 A1 | 5/2009 | Schurr |
| 2009/0142413 A1 | 6/2009 | Allen |
| 2009/0149849 A1 | 6/2009 | Lin |
| 2009/0156590 A1 | 6/2009 | Frank |
| 2009/0171383 A1 | 7/2009 | Cole |
| 2009/0178153 A1 | 7/2009 | Gaitanaris |
| 2009/0182303 A1 | 7/2009 | Walak |
| 2009/0182424 A1 | 7/2009 | Marco |
| 2009/0187200 A1 | 7/2009 | Burnett |
| 2009/0187201 A1 | 7/2009 | Burnett |
| 2009/0196912 A1 | 8/2009 | Eickhoff |
| 2009/0198254 A1 | 8/2009 | Laufer |
| 2009/0214474 A1 | 8/2009 | Jennings |
| 2009/0216262 A1 | 8/2009 | Burnett |
| 2009/0217401 A1 | 8/2009 | Korman |
| 2009/0226907 A1 | 9/2009 | Nice |
| 2009/0227641 A1 | 9/2009 | Bhattacharya |
| 2009/0259240 A1 | 10/2009 | Graham |
| 2009/0264345 A1 | 10/2009 | McAlpine |
| 2009/0275511 A1 | 11/2009 | Dong |
| 2009/0276055 A1 | 11/2009 | Harris |
| 2009/0287231 A1 | 11/2009 | Brooks |
| 2009/0299486 A1 | 12/2009 | Shohat |
| 2009/0299487 A1 | 12/2009 | Stack |
| 2009/0306186 A1 | 12/2009 | Jackson |
| 2009/0317374 A1 | 12/2009 | Park |
| 2010/0004239 A1 | 1/2010 | Tang |
| 2010/0016353 A1 | 1/2010 | Henne |
| 2010/0029615 A1 | 2/2010 | Munchhof |
| 2010/0036481 A1* | 2/2010 | Dubrul et al. ................ 623/1.42 |
| 2010/0048471 A1 | 2/2010 | Kim |
| 2010/0049224 A1 | 2/2010 | Vargas |
| 2010/0068177 A1 | 3/2010 | Faustman |
| 2010/0114150 A1 | 5/2010 | Magal |
| 2010/0121371 A1 | 5/2010 | Brooks |
| 2010/0136114 A1 | 6/2010 | Mao |
| 2010/0137279 A1 | 6/2010 | Cheng |
| 2010/0145301 A1 | 6/2010 | Magal |
| 2010/0150893 A1 | 6/2010 | Faustman |
| 2010/0152765 A1 | 6/2010 | Haley |
| 2010/0158896 A1 | 6/2010 | Brown |
| 2010/0158902 A1 | 6/2010 | Pogue |
| 2010/0168563 A1 | 7/2010 | Braver |
| 2010/0179584 A1 | 7/2010 | Carpenter |
| 2010/0190782 A1 | 7/2010 | Baell |
| 2010/0204093 A1 | 8/2010 | Kaushal |
| 2010/0204221 A1 | 8/2010 | Vankayalapati |
| 2010/0204688 A1 | 8/2010 | Hoey |
| 2010/0209488 A1 | 8/2010 | Wrasidlo |
| 2010/0210622 A1 | 8/2010 | Baell |
| 2010/0221233 A1 | 9/2010 | Borlongan |
| 2010/0222381 A1 | 9/2010 | Vankayalapati |
| 2010/0234435 A1 | 9/2010 | Bhattacharya |
| 2010/0234886 A1 | 9/2010 | Godin |
| 2010/0235197 A1 | 9/2010 | Dang |
| 2010/0247691 A1 | 9/2010 | Kim |
| 2010/0255087 A1 | 10/2010 | Coulter |
| 2010/0256654 A1 | 10/2010 | Pasricha |
| 2010/0256775 A1 | 10/2010 | Belhe |
| 2010/0261162 A1 | 10/2010 | Nice |
| 2010/0266675 A1 | 10/2010 | Gerwick |
| 2010/0268260 A1 | 10/2010 | Riina |
| 2010/0286628 A1* | 11/2010 | Gross ............................ 604/285 |
| 2010/0286660 A1 | 11/2010 | Gross |
| 2010/0298631 A1 | 11/2010 | Stack |
| 2010/0298741 A1 | 11/2010 | Gross |
| 2010/0305590 A1 | 12/2010 | Holmes |
| 2010/0324572 A1 | 12/2010 | Needleman |
| 2010/0324928 A1 | 12/2010 | Dang |
| 2011/0004146 A1 | 1/2011 | Priplata |

(56) References Cited

U.S. PATENT DOCUMENTS

| | | |
|---|---|---|
| 2011/0009801 A1 | 1/2011 | Blaeser |
| 2011/0040230 A1 | 2/2011 | Laufer |
| 2011/0040232 A1 | 2/2011 | Magal |
| 2011/0066175 A1 | 3/2011 | Gross |
| 2011/0068143 A1 | 3/2011 | Laufer |
| 2011/0082535 A1 | 4/2011 | Shin |
| 2011/0092482 A1 | 4/2011 | Nadeson |
| 2011/0097280 A1 | 4/2011 | Dees |
| 2011/0098730 A1 | 4/2011 | Kelleher |
| 2011/0118650 A1 | 5/2011 | Nihalani |
| 2011/0124643 A1 | 5/2011 | Bellevergue |
| 2011/0125211 A1 | 5/2011 | Griffin |
| 2011/0130775 A1 | 6/2011 | Tacchino |
| 2011/0136809 A1 | 6/2011 | Lee |
| 2011/0137428 A1 | 6/2011 | Terliuc |
| 2011/0142905 A1 | 6/2011 | Bar-Shalom |
| 2011/0152608 A1 | 6/2011 | Bachmann |
| 2011/0152899 A1 | 6/2011 | Deem |
| 2011/0166120 A1 | 7/2011 | Luzzio |
| 2011/0172585 A1 | 7/2011 | Weitzner |
| 2011/0185439 A1 | 7/2011 | Gaitanaris |
| 2011/0190905 A1 | 8/2011 | Behan |
| 2011/0206760 A1 | 8/2011 | Kliger |
| 2011/0213469 A1 | 9/2011 | Chin |
| 2011/0214189 A1 | 9/2011 | Gaitanaris |
| 2011/0218143 A1 | 9/2011 | Kaushal |
| 2011/0218563 A1 | 9/2011 | Brooks |
| 2011/0245752 A1 | 10/2011 | Levine |
| 2011/0256123 A1 | 10/2011 | Ilan |
| 2011/0257580 A1 | 10/2011 | Meade |
| 2011/0263504 A1 | 10/2011 | Cerami |
| 2011/0269772 A1 | 11/2011 | Bearss |
| 2011/0270405 A1 | 11/2011 | Geitz |
| 2011/0270410 A1 | 11/2011 | Stack |
| 2011/0275891 A1 | 11/2011 | Shemi |
| 2011/0276091 A1 | 11/2011 | Melanson |
| 2011/0288080 A1 | 11/2011 | SaulnierSholler |
| 2011/0295054 A1 | 12/2011 | Aldridge |
| 2011/0295055 A1 | 12/2011 | Albrecht |
| 2011/0295151 A1 | 12/2011 | Bakos |
| 2011/0295286 A1 | 12/2011 | Harris |
| 2011/0301156 A1 | 12/2011 | Frank |
| 2011/0301353 A1 | 12/2011 | Tang |
| 2011/0307075 A1 | 12/2011 | Sharma |
| 2011/0320219 A1 | 12/2011 | Dang |
| 2012/0003204 A1 | 1/2012 | Park |
| 2012/0003634 A1 | 1/2012 | Frumkin |
| 2012/0004676 A1 | 1/2012 | Vargas |
| 2012/0029550 A1 | 2/2012 | Forsell |
| 2012/0041465 A1 | 2/2012 | Shalon |
| 2012/0046718 A1 | 2/2012 | Singh |
| 2012/0058107 A1 | 3/2012 | Tang |
| 2012/0059431 A1 | 3/2012 | Williams |
| 2012/0065571 A1 | 3/2012 | Thompson |
| 2012/0083819 A1 | 4/2012 | Wang |
| 2012/0087910 A1 | 4/2012 | Trieu |
| 2012/0088300 A1 | 4/2012 | Melton |
| 2012/0088967 A1 | 4/2012 | Laufer |
| 2012/0089170 A1 | 4/2012 | Dominguez |
| 2012/0095384 A1 | 4/2012 | Babkes |
| 2012/0095385 A1 | 4/2012 | Dominguez |
| 2012/0095483 A1 | 4/2012 | Babkes |
| 2012/0095494 A1 | 4/2012 | Dominguez |
| 2012/0095497 A1 | 4/2012 | Babkes |
| 2012/0108590 A1 | 5/2012 | Birtalan |
| 2012/0110682 A1 | 5/2012 | Mather |
| 2012/0116286 A1 | 5/2012 | Williams |
| 2012/0121594 A1 | 5/2012 | Smith |
| 2012/0142760 A1 | 6/2012 | Kieffer |
| 2012/0148540 A1 | 6/2012 | Freeman |
| 2012/0157470 A1 | 6/2012 | Catron |
| 2012/0157495 A1 | 6/2012 | Munchhof |
| 2012/0158026 A1 | 6/2012 | Behan |
| 2012/0179086 A1 | 7/2012 | Shank |
| 2012/0184541 A1 | 7/2012 | Baell |
| 2012/0184893 A1 | 7/2012 | Thompson |
| 2012/0184967 A1 | 7/2012 | Levine |
| 2012/0208786 A1 | 8/2012 | Lyles |
| 2012/0209400 A1 | 8/2012 | Schurr |
| 2012/0213731 A1 | 8/2012 | Faustman |
| 2012/0214848 A1 | 8/2012 | Zhang |
| 2012/0215152 A1 | 8/2012 | Levine |
| 2012/0232460 A1 | 9/2012 | Raven |
| 2012/0232577 A1 | 9/2012 | Birk |
| 2012/0245087 A1 | 9/2012 | Jackson |
| 2012/0245553 A1 | 9/2012 | Raven |
| 2012/0253259 A1 | 10/2012 | Belhe |
| 2012/0253260 A1 | 10/2012 | Belhe |
| 2012/0253529 A1 | 10/2012 | Carlson |
| 2012/0258126 A1 | 10/2012 | Scholler |
| 2012/0263781 A1 | 10/2012 | Chancellor |
| 2012/0271217 A1 | 10/2012 | Stack |
| 2012/0277210 A1 | 11/2012 | Catron |
| 2012/0277271 A1 | 11/2012 | Nadeson |
| 2012/0301475 A1 | 11/2012 | Shemesh |
| 2012/0302602 A1 | 11/2012 | Frank |
| 2012/0309775 A1 | 12/2012 | Cheng |
| 2013/0005724 A1 | 1/2013 | Lassalle |
| 2013/0005964 A1 | 1/2013 | Luzzio |
| 2013/0006382 A1 | 1/2013 | Behan |
| 2013/0006672 A1 | 1/2013 | Dang |
| 2013/0011332 A1 | 1/2013 | Boyden |
| 2013/0013084 A1 | 1/2013 | Birk |
| 2013/0030350 A1 | 1/2013 | Albrecht |
| 2013/0030351 A1 | 1/2013 | Belhe |
| 2013/0034844 A1 | 2/2013 | Boyle |
| 2013/0035576 A1 | 2/2013 | OGrady |
| 2013/0041424 A1 | 2/2013 | Neisz |
| 2013/0071466 A1 | 3/2013 | Chancellor |
| 2013/0079329 A1 | 3/2013 | Hood |
| 2013/0079345 A1 | 3/2013 | Eickhoff |
| 2013/0079603 A1 | 3/2013 | Vargas |
| 2013/0133091 A1 | 5/2013 | Korman |
| 2013/0156726 A1 | 6/2013 | Ichim |
| 2013/0164371 A1 | 6/2013 | Imran |
| 2013/0164372 A1 | 6/2013 | Imran |
| 2013/0164373 A1 | 6/2013 | Imran |
| 2013/0165372 A1 | 6/2013 | Imran |
| 2013/0165373 A1 | 6/2013 | Imran |
| 2013/0165772 A1 | 6/2013 | Traverso |
| 2013/0165859 A1 | 6/2013 | Imran |
| 2013/0171244 A1 | 7/2013 | Imran |
| 2013/0171245 A1 | 7/2013 | Imran |
| 2013/0171246 A1 | 7/2013 | Imran |
| 2013/0171247 A1 | 7/2013 | Imran |
| 2013/0172257 A1 | 7/2013 | Imran |
| 2013/0177527 A1 | 7/2013 | Imran |
| 2013/0177550 A1 | 7/2013 | Imran |
| 2013/0178472 A1 | 7/2013 | Bellevergue |
| 2013/0189240 A1 | 7/2013 | Cho |
| 2013/0189353 A1 | 7/2013 | Imran |
| 2013/0190675 A1 | 7/2013 | Sandoski |
| 2013/0195970 A1 | 8/2013 | Imran |
| 2013/0197421 A1 | 8/2013 | Sharvit |
| 2013/0204208 A1 | 8/2013 | Olson |
| 2013/0210800 A1 | 8/2013 | Nair |
| 2013/0218289 A1 | 8/2013 | Gao |
| 2013/0245068 A1 | 9/2013 | Kwon |
| 2013/0247233 A1 | 9/2013 | Gaitanaris |
| 2013/0253408 A1 | 9/2013 | Krueger |
| 2013/0273061 A1 | 10/2013 | Huang |
| 2013/0274659 A1 | 10/2013 | Imran |
| 2013/0274789 A1 | 10/2013 | Brooks |
| 2013/0281911 A1 | 10/2013 | Babkes |
| 2013/0289139 A1 | 10/2013 | Radford |
| 2013/0289466 A1 | 10/2013 | Babkes |
| 2013/0296764 A1 | 11/2013 | Stack |
| 2013/0296913 A1 | 11/2013 | Foote |
| 2013/0310727 A1 | 11/2013 | Stack |
| 2013/0310833 A1 | 11/2013 | Brown |
| 2013/0324902 A1 | 12/2013 | Miller |
| 2013/0324906 A1 | 12/2013 | Neisz |
| 2013/0324907 A1 | 12/2013 | Huntley |
| 2013/0331359 A1 | 12/2013 | Yun |

(56) References Cited

U.S. PATENT DOCUMENTS

| | | |
|---|---|---|
| 2013/0331383 A1 | 12/2013 | SaulnierSholler |
| 2013/0331759 A1 | 12/2013 | Neisz |
| 2013/0337563 A1 | 12/2013 | Phan |
| 2013/0338741 A1 | 12/2013 | Singh |
| 2013/0344173 A1 | 12/2013 | Fogelman |
| 2013/0345670 A1 | 12/2013 | Rajagopalan |
| 2014/0004175 A1 | 1/2014 | Kliger |
| 2014/0005190 A1 | 1/2014 | Baell |
| 2014/0018719 A1 | 1/2014 | Chamorro |
| 2014/0024114 A1 | 1/2014 | Melton |
| 2014/0024991 A1 | 1/2014 | Chin |
| 2014/0039250 A1 | 2/2014 | Bachmann |
| 2014/0044641 A1 | 2/2014 | Toporik |
| 2014/0044736 A1 | 2/2014 | Hammers |
| 2014/0045815 A1 | 2/2014 | Hood |
| 2014/0051645 A1 | 2/2014 | Matschiner |
| 2014/0081416 A1 | 3/2014 | Clerc |
| 2014/0094734 A1 | 4/2014 | Stack |
| 2014/0142720 A1 | 5/2014 | Stack |
| 2014/0180188 A1 | 6/2014 | Chin |
| 2014/0180192 A1 | 6/2014 | Ortiz |
| 2014/0194806 A1 | 7/2014 | Belhe |
| 2014/0194917 A1 | 7/2014 | Sharma |
| 2014/0200502 A1 | 7/2014 | Belhe |
| 2014/0213960 A1 | 7/2014 | Belhe |
| 2014/0221899 A1 | 8/2014 | Vargas |
| 2014/0243992 A1 | 8/2014 | Walsh |
| 2015/0196412 A1 | 7/2015 | Roselauf |

FOREIGN PATENT DOCUMENTS

| | | |
|---|---|---|
| AU | 2012211067 A1 | 8/2013 |
| AU | 2010232570 B2 | 11/2013 |
| AU | 2014200766 A1 | 3/2014 |
| AU | 2012315575 A1 | 4/2014 |
| CA | 2756991 A1 | 10/2010 |
| CN | 1713870 | 2/2003 |
| CN | 1575155 | 2/2005 |
| CN | 102387762 A | 3/2012 |
| CN | 102470038 A | 5/2012 |
| CN | 103635212 | 3/2014 |
| CN | 103635212 A | 3/2014 |
| EP | 0278937 B1 | 10/1993 |
| EP | 0480667 B1 | 3/1996 |
| EP | 0774571 | 5/1997 |
| EP | 0754017 B1 | 6/2002 |
| EP | 0843538 B1 | 6/2002 |
| EP | 1420730 | 5/2004 |
| EP | 1492477 | 1/2005 |
| EP | 1492478 | 1/2005 |
| EP | 2413849 A1 | 2/2012 |
| EP | 2451411 A2 | 5/2012 |
| EP | 2521513 A1 | 11/2012 |
| EP | 2667910 A2 | 12/2013 |
| EP | 2413849 B1 | 7/2014 |
| EP | 2760502 A1 | 8/2014 |
| JP | 04212348 | 8/1992 |
| KR | 20120008492 A | 1/2012 |
| WO | 1988000027 | 1/1988 |
| WO | 1991001117 | 2/1991 |
| WO | 1994001165 A1 | 1/1994 |
| WO | 0012027 | 3/2000 |
| WO | 2000012027 | 3/2000 |
| WO | 0032137 | 6/2000 |
| WO | 2000032137 | 6/2000 |
| WO | 0042949 | 7/2000 |
| WO | 0145485 A2 | 6/2001 |
| WO | 2001049359 | 7/2001 |
| WO | 02096327 A2 | 12/2002 |
| WO | 03017882 A2 | 3/2003 |
| WO | 03086246 A1 | 10/2003 |
| WO | 03086247 A1 | 10/2003 |
| WO | 03086360 A1 | 10/2003 |
| WO | 03094784 A2 | 11/2003 |
| WO | 03094785 A1 | 11/2003 |
| WO | 2003094784 | 11/2003 |
| WO | 2004049982 | 6/2004 |
| WO | 2004064680 A1 | 8/2004 |
| WO | 2004064685 A1 | 8/2004 |
| WO | 2004069331 A2 | 8/2004 |
| WO | 2004069332 A1 | 8/2004 |
| WO | 2004087014 A2 | 10/2004 |
| WO | 2004087233 A2 | 10/2004 |
| WO | 06064503 A2 | 6/2006 |
| WO | 2007007339 A2 | 1/2007 |
| WO | 2008023374 A2 | 2/2008 |
| WO | WO2008/112894 | 9/2008 |
| WO | 2008121409 A1 | 10/2008 |
| WO | 2008121831 A1 | 10/2008 |
| WO | 2008154450 A1 | 12/2008 |
| WO | 2010115011 A1 | 10/2010 |
| WO | 2010128495 A1 | 11/2010 |
| WO | 2011006098 A2 | 1/2011 |
| WO | 2011085234 A1 | 7/2011 |
| WO | 2011159271 | 12/2011 |
| WO | 2011159271 A1 | 12/2011 |
| WO | 2012068377 A1 | 5/2012 |
| WO | 2012103531 A2 | 8/2012 |
| WO | 2013049779 A1 | 4/2013 |
| WO | 2014113483 A1 | 7/2014 |
| WO | 2014153267 | 9/2014 |
| WO | 2016049149 A2 | 3/2016 |
| WO | WO2017/132676 | 8/2017 |

OTHER PUBLICATIONS

International Search Report for PCT/US2010/038444, dated Sep. 16, 2010.
International Search Report for PCT/US2003/038238, dated Oct. 14, 2004.
International Search Report for PCT/US2002/027177, dated Feb. 14, 2003.
First Office Action for Application No. CN 201080068476, dated Sep. 2, 2014.
Second Office Action for Application No. CN 201080068476, dated Jun. 3, 2015.
Third Office Action for Application No. CN 201080068476, dated Nov. 13, 2015.
Supplementary Partial European Search Report for EP20100853335, dated Nov. 5, 2014.
Klausner et al., "Expandable gastroretentive dosage forms", Journal of Controlled Release 90:143-162 (2003).
Sun et al., "Intestinal electric stimulation decreases fat absorption in rats: Therapeutic potential for obesity", Obes Res. Aug. 2004; 12(8):1235-42.
Office Action dated May 29, 2012 for U.S. Appl. No. 12/814,481.
Office Action dated Jan. 4, 2013 for U.S. Appl. No. 12/814,481.
Notice of Allowance dated Sep. 30, 2013 for U.S. Appl. No. 12/814,481.
International Search Report for PCT/US2014/029846, dated Apr. 2, 2015.
International Search Report for PCT/US2015/051668, dated Apr. 19, 2016.
European Application No. 18162640.1—Search Report dated Apr. 16, 2018.

* cited by examiner

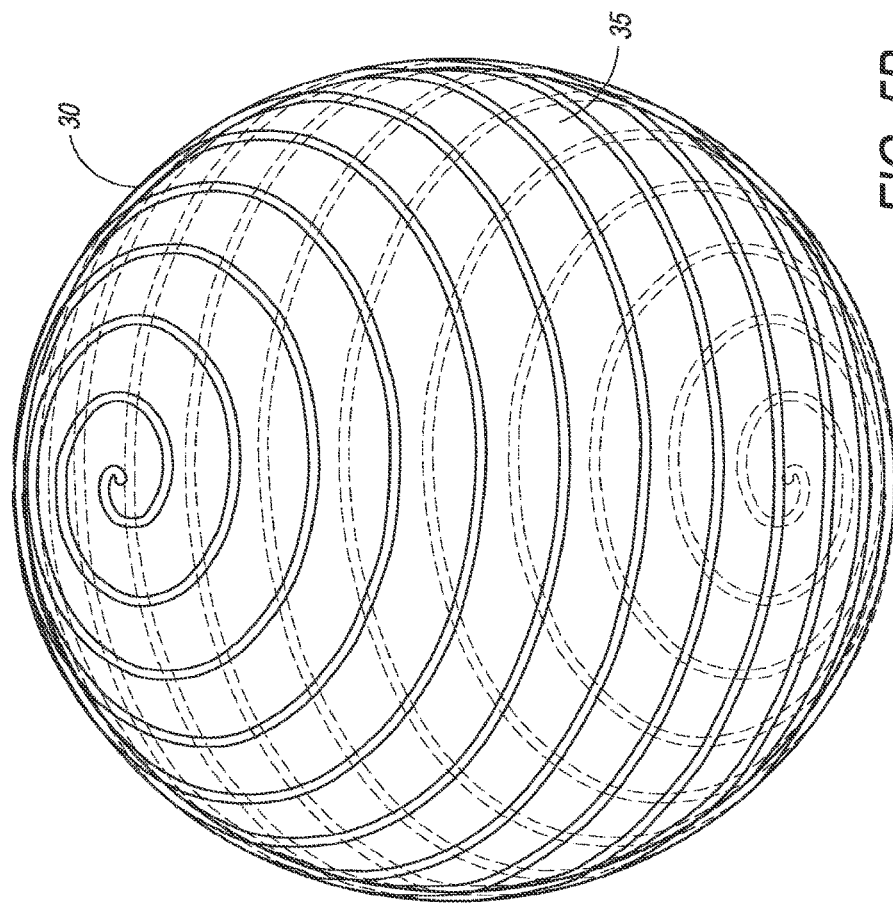
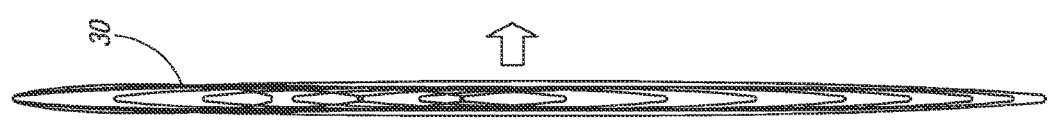
FIG. 5B
FIG. 5A

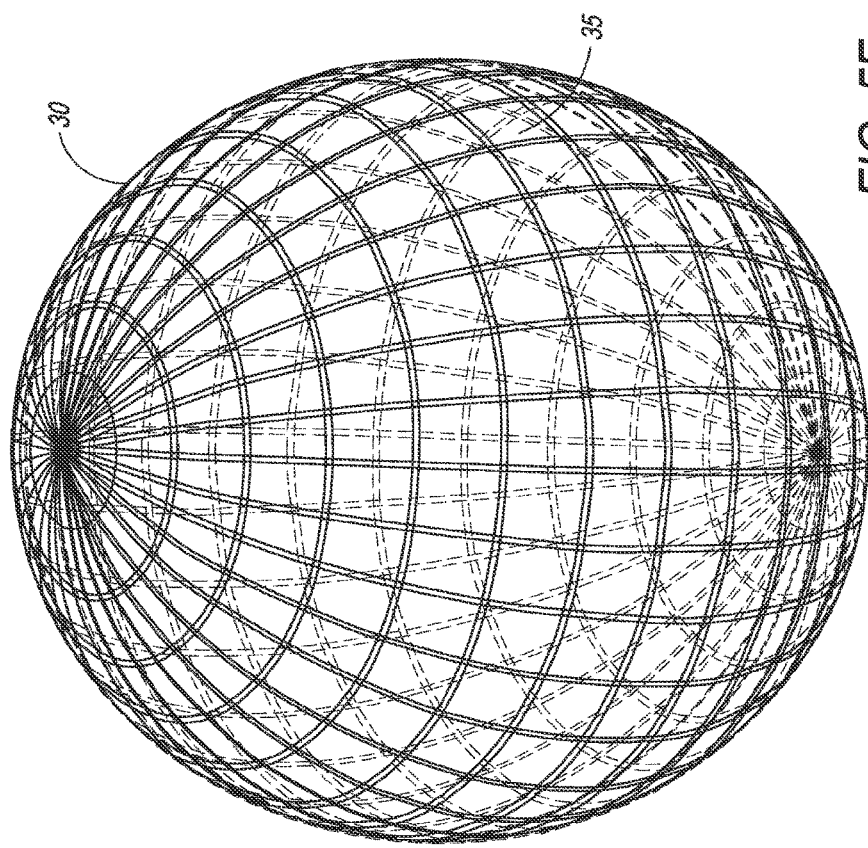
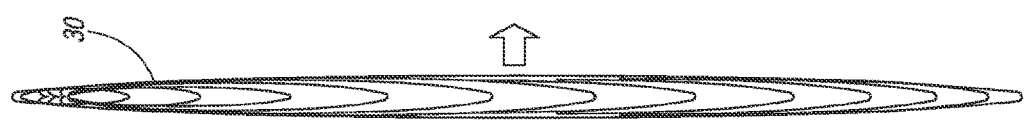
FIG. 5E
FIG. 5F

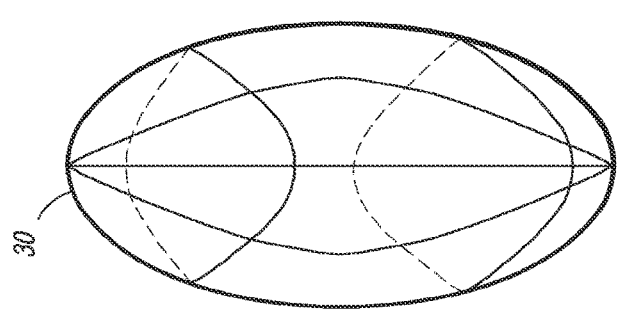
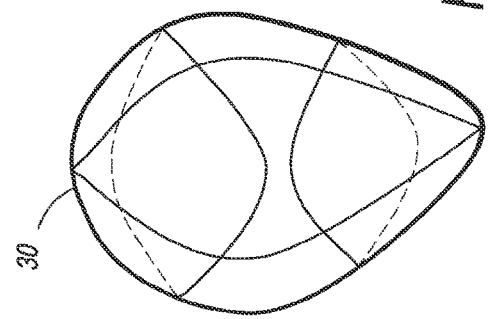
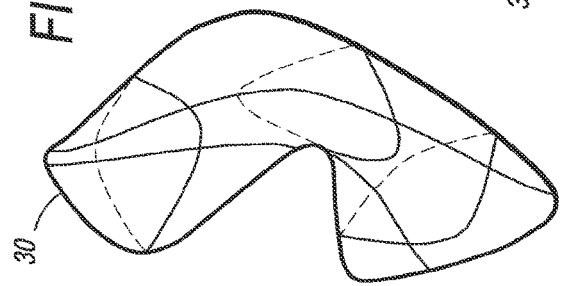
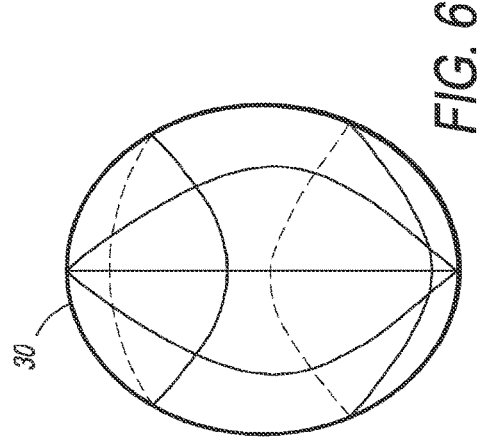
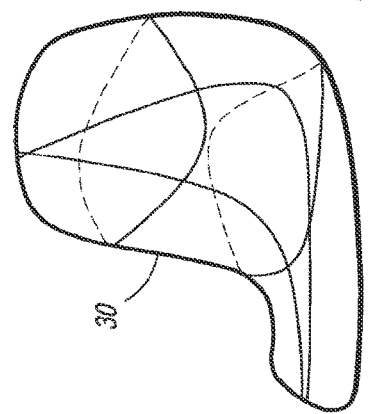
FIG. 6
FIG. 6A
FIG. 6B
FIG. 6C
FIG. 6D

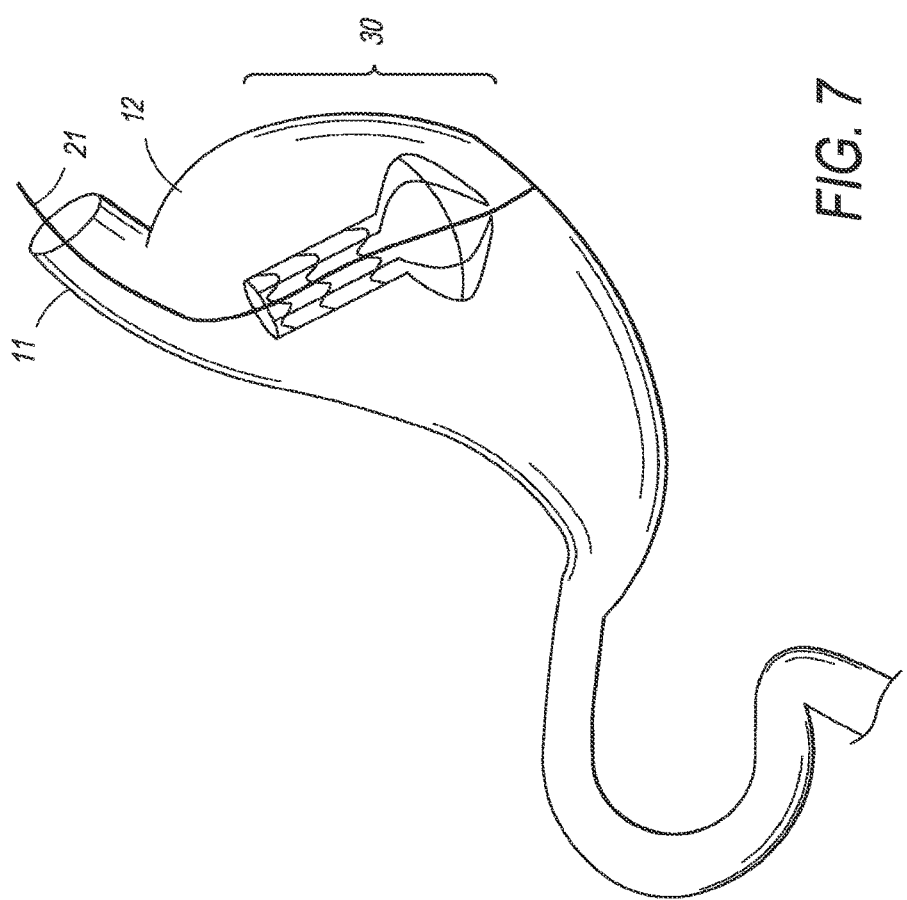

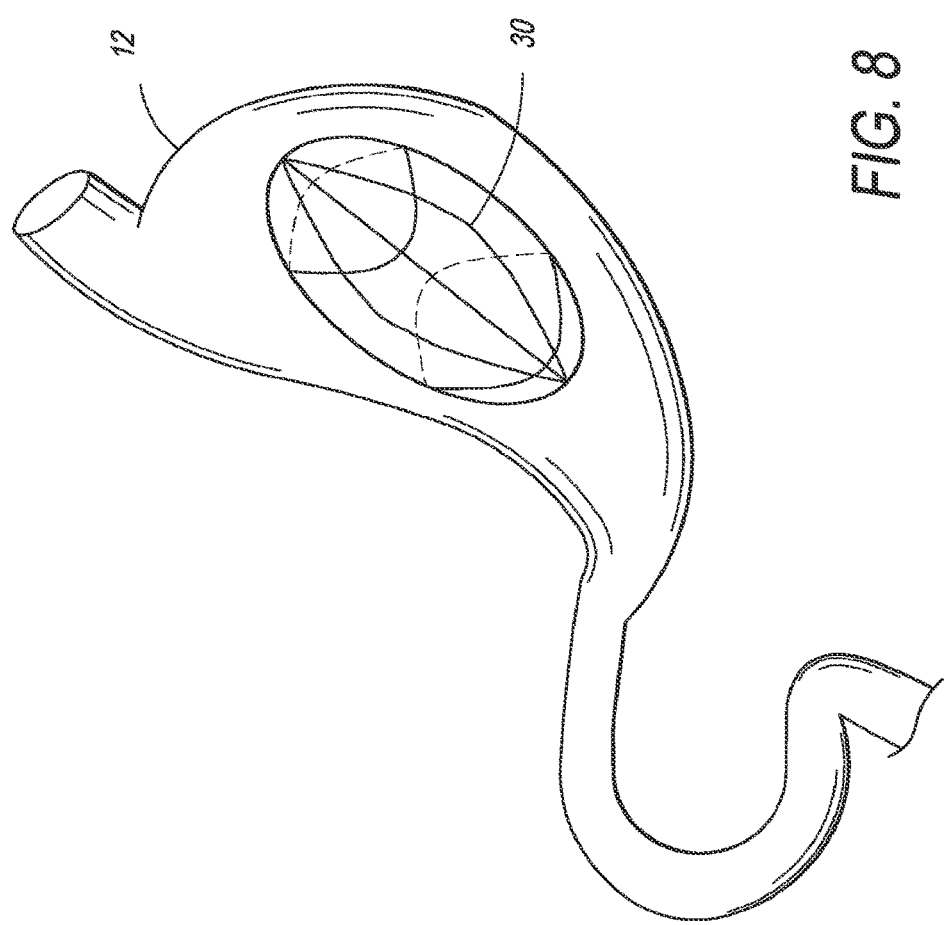

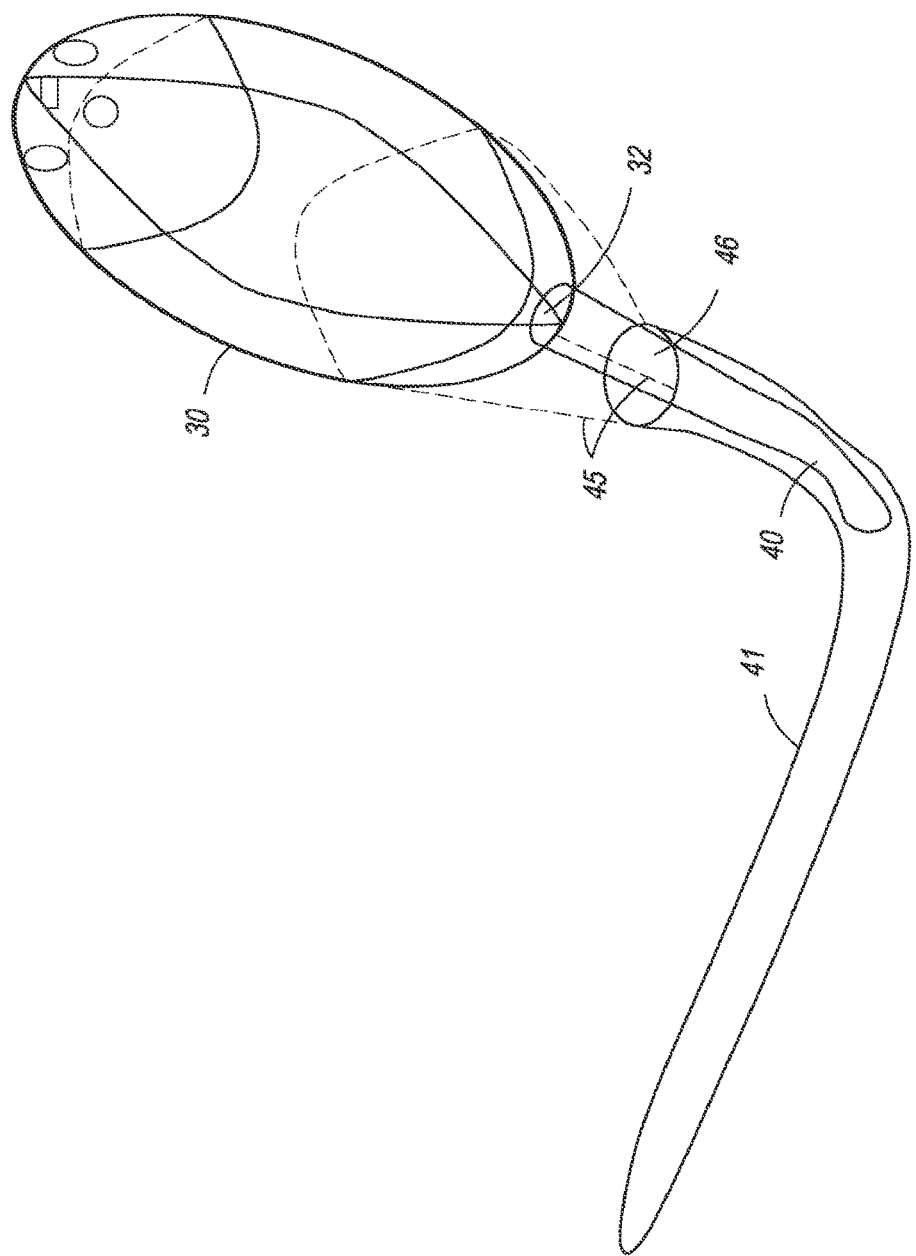

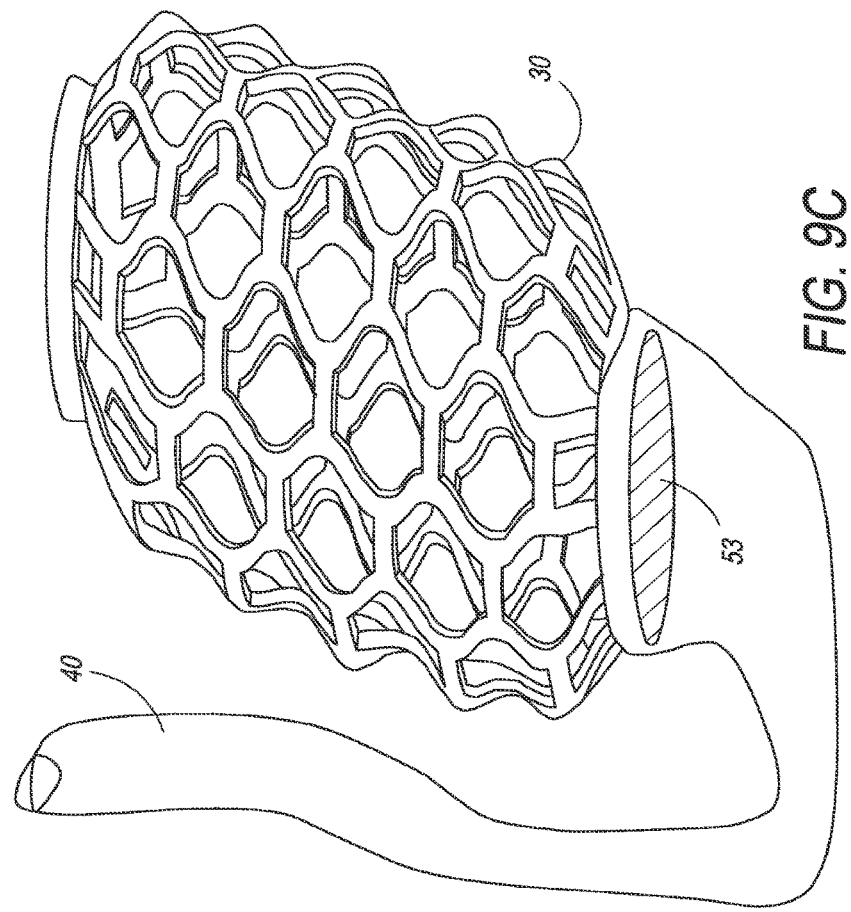
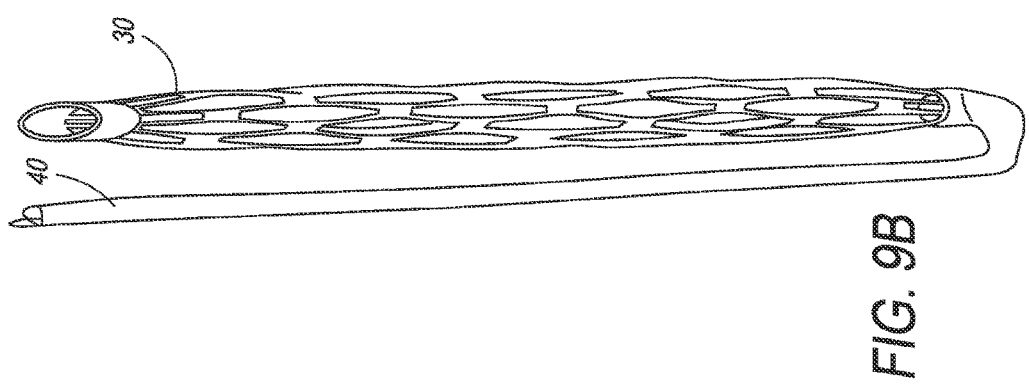

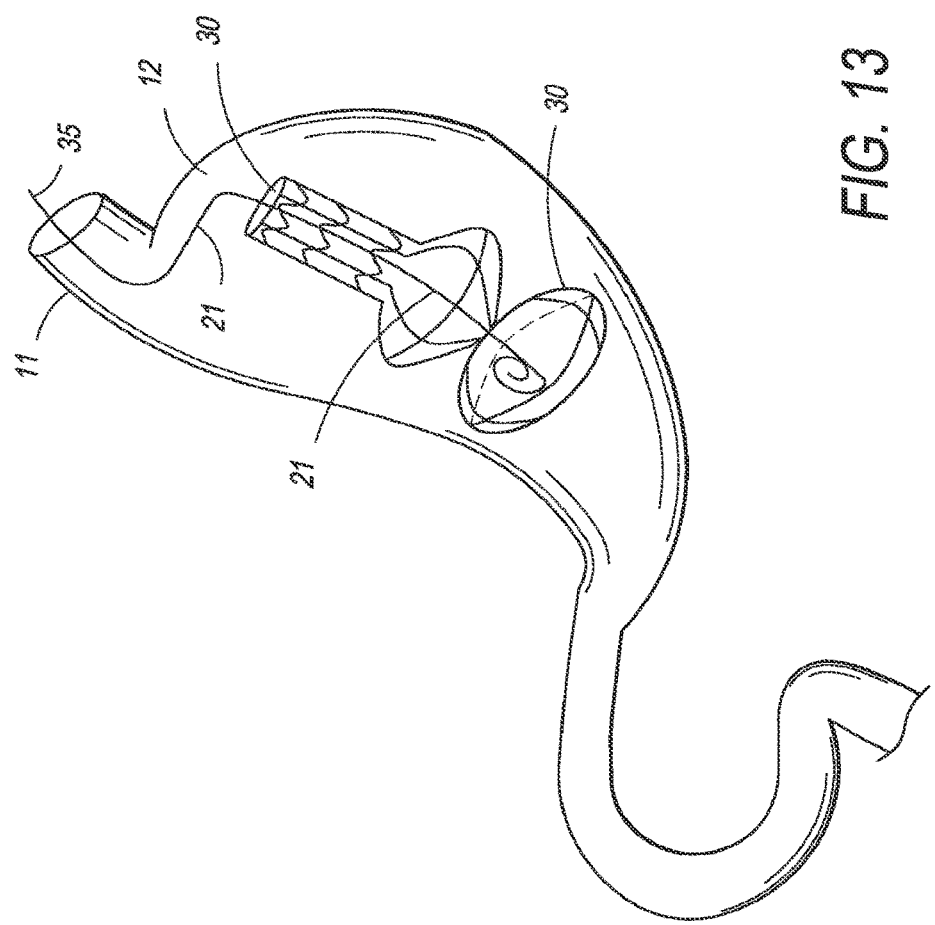

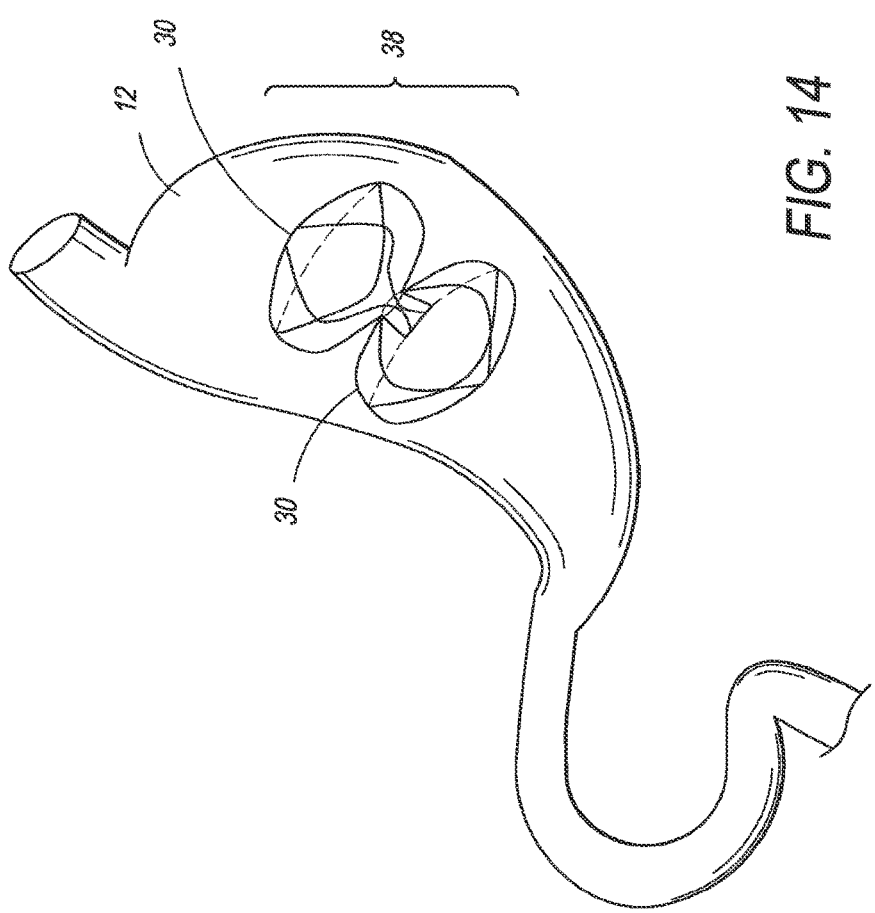

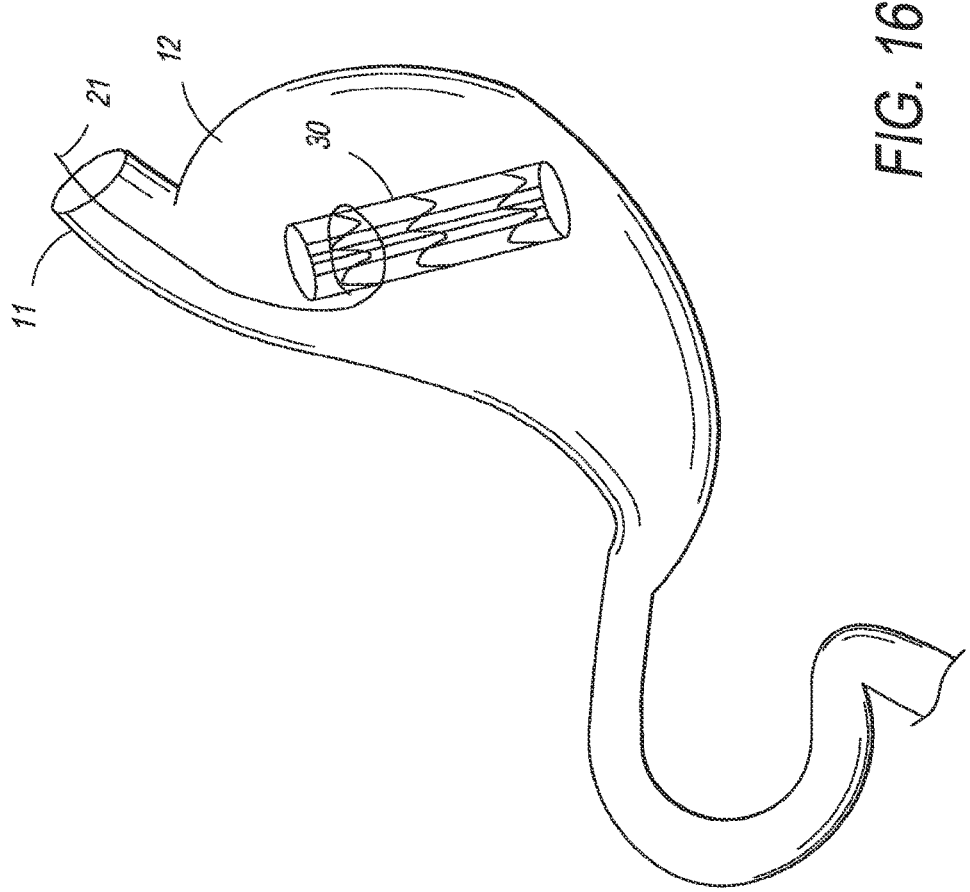

INTRAGASTRIC DEVICE FOR TREATING OBESITY

CROSS-REFERENCE

The present application is a continuation of U.S. patent application Ser. No. 12/814,481, entitled "Intragastric Device for Treating Obesity" and filed on Jun. 13, 2010, which is hereby incorporated by reference in its entirety.

FIELD OF THE INVENTION

The present invention relates to a medical device useful in the treatment of obesity. More particularly, the present invention relates to an intragastric device of dynamic weight that reduces gastric volume and slows gastric emptying, thereby inducing satiety leading to patient weight loss.

BACKGROUND OF THE INVENTION

Obesity is a common condition and major public health problem in developed nations including the United States. As of 2009, more than two thirds of American adults, approximately 127 million people, were either overweight or obese. Data suggest that 300,000 Americans die prematurely from obesity-related complications each year. Many children in the United States are also either overweight or obese. Hence, the overall number of overweight Americans is expected to rise in the future. It has been estimated that obesity costs the United States approximately $100 billion annually in direct and indirect health care expenses and in lost productivity. This trend is also apparent in many other developed nations.

For adults, the body mass index (BMI) is used to determine if one is overweight or obese. A person's BMI is calculated by multiplying body weight in pounds by 703 and then dividing the total by height in inches squared. A person's BMI is expressed as kilograms per meter squared. An adult is considered overweight if his or her BMI is between 25 and 30 kg/m2. Obesity is defined as possessing a BMI between 30 and 40 kg/m2. A BMI greater than 30 kg/m2 is associated with significant co-morbidities. Morbid obesity is defined as possessing either a body weight more than 100 pounds greater than ideal or a BMI greater than 40 kg/m2. Approximately 5% of the U.S. population meets at least one of the criteria for morbid obesity. Morbid obesity is associated with many diseases and disorders including, for example: diabetes; hypertension; heart attack; stroke; dyslipidemia; sleep apnea; pickwickian syndrome; asthma; lower back and disc disease; weight-bearing osteoarthritis of the hips, knees, ankles and feet; thrombophlebitis and pulmonary emboli; intertriginous dermatitis; urinary stress incontinence; gastroesophageal reflux disease (GERD); gallstones; and, sclerosis and carcinoma of the liver. In women, infertility, cancer of the uterus, and cancer of the breast are additionally associated with morbid obesity. Taken together, the diseases associated with morbid obesity markedly reduce the odds of attaining an average lifespan. The sequelae raise annual mortality rates in affected people by a factor of 10 or more.

Current treatments for obesity include diet, exercise, behavioral treatments, medications, surgery (open and laparoscopic), and endoscopic devices. New drug treatments for obesity are currently being evaluated in clinical trials. However, a high efficacy pharmaceutical treatment has not yet been developed. Further, short-term and long-term side effects of current pharmaceutical treatments often concern consumers, pharmaceutical providers, and/or their insurers. Generally, diet or drug therapy programs have been consistently disappointing, failing to bring about significant, sustained weight loss in the majority of morbidly obese people.

Currently, most operations used to treat morbid obesity include gastric restrictive procedures, involving the creation of a small (e.g., 15-35 ml) upper gastric pouch that drains through a small outlet (e.g., 0.75-1.2 cm), setting in motion the body's satiety mechanism. About 15% of operations used to treat morbid obesity performed in the United States involve combining a gastric restrictive procedure with a malabsorptive procedure. Typical malabsorptive procedures divide small intestinal flow into a biliary-pancreatic conduit and a food conduit. Potential long-term side effects associated with abdominal surgical procedures include herniation and small bowel obstruction. In addition, long-term problems specific to bariatric procedures also include gastric outlet obstruction, marginal ulceration, protein malnutrition, and vitamin deficiency.

Other surgical strategies for treating obesity include endoscopic procedures, many of which are still in development. Endoscopic procedures and devices to produce gastric pouch and gastrojejunal anastomosis are used to replicate laparoscopic procedures. Endoscopically placed gastric balloons restrict gastric volume and result in satiety with smaller meals. For example, U.S. Pat. No. 7,172,613, assigned to Districlass Medical SA, describes "An intragastric device inserted by endoscopic path into a patient's stomach. The device includes a balloon or envelope having a specific nominal volume. The balloon is sealingly connected to connecting elements consisting of a disc forming a support base for the balloon against an inner wall of the stomach. The device also includes a flexible tube or catheter for connecting the balloon to a filling device and catching element integral with the tube or catheter. The connection elements enable a doctor to set and/or remove the balloon and to fix, either inside the patient's body, or subcutaneously the filling device and to be able to bring the balloon or envelope to its predetermined nominal volume."

The silicon intragastric balloon (IGB) has been developed as a temporary aid to achieve weight loss specifically for people who weigh 40% or more of their ideal weight and who have had unsatisfactory results in their treatment of obesity, despite being cared for by a multidisciplinary team. This treatment is also indicated for morbidly obese patients who have a high morbidity and mortality risk for surgery. The placement and removal of the IGB is an endoscopic procedure and the balloon is designed to float freely inside the stomach. The IGB technique reduces the volume of the stomach and leads to a premature feeling of satiety. However, use of IGBs did not show convincing evidence of a greater weight loss. The relative risks for minor complications, for example, gastric ulcers and erosions, were significantly raised. All inflatable IGB devices suffer from the problem of deterioration of the balloon over time. This deterioration can result in deflation with loss of efficacy and complications such as small bowel obstruction secondary to balloon migration. Due to loss of efficacy over time, IGB devices are recommended only for short (<6 month) durations. In addition, rapid inflation of the balloon poses the risk of esophageal or gastric perforations, both of which are surgical emergencies. Deaths have been reported in patients using IGB treatment.

Endoscopic procedures are also used to deploy mesh structures into the stomach in an effort to occupy stomach volume and create the artificial sensation of being full. For example, United States Patent Application Number 2007098039, assigned to Wilson-Cook Medical, Inc., describes "An intragastric device generally comprises a strip digestive-resistant mesh material that is operable between a first configuration and a second configuration. The first configuration is sufficiently small to permit introduction of the digestive-resistant mesh material into a gastric lumen of the mammal. The second configuration is sufficiently large to prevent the digestive-resistant mesh material from passing through the mammal's pylorus, thereby permitting the mesh member to act as an artificial bezoar."

Although endoscopically placed balloon structures can be effective, they are not without their associated risks and complications. Mesh structures are effective in occupying available gastric volume but they do not address gastric emptying. Migration and small bowel obstruction from such devices continue to remain a significant problem. Therefore, a need exists for an intragastric device to treat obesity that combines the benefits obtained through reducing stomach volume and slowing gastric emptying while remaining relatively safe. This device should limit side effects and be able to be deployed and removed in a non-invasive manner with relative ease. In addition, this new device should have the option of further treating obesity by including the benefits obtained by malabsorptive diversion procedures. The addition of this optional benefit would make the device effective in treating not only obesity, but type II diabetes as well.

SUMMARY OF THE INVENTION

The present invention is directed toward an intragastric device having a top and a bottom comprising: a structure having a pre-deployment shape with a first volume and a post-deployment shape with a second volume, wherein said first volume is less than said second volume; wherein, in said post-deployment shape, said device comprises at least one first opening proximate to the top of said device, each first opening defined by an area where a sum of the areas of the first openings is equal to a first area; wherein, in said post-deployment shape, said device comprises at least one second opening proximate to the bottom of said device, each second opening defined by an area where a sum of the areas of the second openings is equal to a second area; and wherein said first area is equal or larger than said second area. Optionally, the pre-deployment shape is linear, cylindrical, conical, a non-linear cylinder, spherical, a cube or a cuboid. Optionally, the structure comprises at least one of a mesh structure, a spiral structure, or a lattice structure.

Optionally, the wire mesh has a plurality of vertical and horizontal elements which, when expanded, create the at least one first opening and the at least one second opening. The wire mesh vertical and horizontal elements comprise at least one of a metal, an alloy, a polymer, a shape memory metal, or a shape memory polymer. The structure in enveloped by a partially perforated membrane having a surface area. The membrane comprises at least one of latex, parylene, polyurethane, polytetrafluoroethylene [PTFE], fluorinated ethylene-propylene, Dacron, or Polyethylene terephthalate (PET). The membrane has at least one first membrane opening, each first membrane opening having a first membrane opening area where a sum of said first membrane opening areas is equal to a third area, wherein said at least one first membrane opening is proximate to the top of the device.

The membrane has at least one second membrane opening, each second membrane opening having a second membrane opening area where a sum of said second membrane opening areas is equal to a fourth area, wherein said at least one second membrane opening is proximate to the bottom of the device and wherein the third area is equal or larger than the fourth area. The sum of said third area and fourth area is between one and ninety-nine percent of the membrane surface area. The membrane comprises at least one opening and wherein said opening has at least one valve that controls a directionality of flow of food or nutrients in and out of the device.

Optionally, the device is attached to a catheter, wherein said catheter is configured to induce a change from the pre-deployment shape to said post-deployment shape. A sleeve is attached to the bottom of said device, wherein said sleeve has a length sufficient to extend from the bottom of the device, through a patient's pylorus and duodenum, and into the patient's jejunum. The sleeve comprises at least one of latex, parylene, polyurethane, polytetrafluoroethylene [PTFE], fluorinated ethylene-propylene, Dacron, or Polyethylene terephthalate (PET). The device is configured to receive a second intragastric device.

In another embodiment, the present invention is directed toward an intragastric device having a top and a bottom comprising: a structure having a pre-deployment shape with a first volume and a post-deployment shape with a second volume, wherein said first volume is less than said second volume; wherein, in said post-deployment shape, said device comprises a plurality of first openings, each of said plurality of first openings defined by an area where a sum of the areas of the plurality of first openings is equal to a first area; wherein, in said post-deployment shape, said device comprises a plurality of second openings, each of said plurality of second openings defined by an area where a sum of the areas of the plurality of second openings is equal to a second area; wherein said first area is equal to larger than said second area; wherein said first area is closer to the top of device relative to the second area; and wherein said structure is enveloped by a membrane that does not cover said first area or said second area.

In another embodiment, the present invention is directed toward an intragastric device having a top and a bottom comprising: a structure having a pre-deployment shape with a first volume and a post-deployment shape with a second volume, wherein said first volume is less than said second volume; wherein, in said post-deployment shape, said device comprises at least one first opening to allow for entry of food into the device and at least one second opening to allow for exit of food from the device, wherein the device has a first weight when a patient is in a pre-feeding stage and a second weight when a patient is in a feeding or a post-feeding stage, and wherein the second weight is greater than the first weight. A patient is in a feeding stage when a patient is actively ingesting food or nutrients. This stage typically lasts between 1 minute and 1 hour. A patient is in a post-feeding stage after the patient has stopped ingesting food or nutrients and till most of the food or nutrients have exited the stomach. This stage normally lasts between 15 minutes and 4 hours and depends upon amount and type of food or nutrients ingested. This state is also affected by the health of patient and can be significantly prolonged in patients having gastric emptying abnormalities such as gastroparesis. A patient is in a pre-feeding stage between the end of post-feeding stage and the beginning of the feeding stage. The first opening is the same as the second opening. The first opening is different from the second opening. The device has a top half with a first weight and a bottom half with a second weight and wherein the first weight is different from the second weight.

BRIEF DESCRIPTION OF THE DRAWINGS

These and other features and advantages of the present invention will be appreciated as they become better understood by reference to the following detailed description when considered in connection with the accompanying drawings, wherein:

FIG. 5A is an illustration of another embodiment of the intragastric device in an exemplary pre-deployment configuration;

FIG. 5B is an illustration of the intragastric device of FIG. 5A in an exemplary post-deployment configuration;

FIG. 5E is an illustration of yet another embodiment of the intragastric device in an exemplary pre-deployment configuration;

FIG. 5F is an illustration of the intragastric device of FIG. 5E in an exemplary post-deployment configuration;

FIG. 6 is an illustration of one embodiment depicting a first exemplary configuration of the intragastric device post-deployment;

FIG. 6A is an illustration of one embodiment depicting a second exemplary configuration of the intragastric device post-deployment;

FIG. 6B is an illustration of one embodiment depicting a third exemplary configuration of the intragastric device post-deployment;

FIG. 6C is an illustration of one embodiment depicting a fourth exemplary configuration of the intragastric device post-deployment;

FIG. 6D is an illustration of one embodiment depicting another exemplary configuration of the intragastric device post-deployment;

FIG. 7 is an illustration of one embodiment of an intragastric device being deployed in the stomach;

FIG. 8 is an illustration of one embodiment of a fully deployed intragastric device in the stomach;

FIG. 9 is an illustration of one embodiment of an intragastric device with an attached sleeve;

FIG. 9B is an illustration of another embodiment of the intragastric device with an attached sleeve in an exemplary pre-deployment configuration;

FIG. 9C is an illustration of the intragastric device with an attached sleeve of FIG. 9B in an exemplary post-deployment configuration;

FIG. 13 is an illustration of one single exemplary intragastric device being attached to a previously deployed single intragastric device in the stomach;

FIG. 14 is an illustration of an exemplary fully deployed combined intragastric device in the stomach;

FIG. 16 is an illustration of an exemplary intragastric device being removed from the stomach;

DETAILED DESCRIPTION

Figure 1:
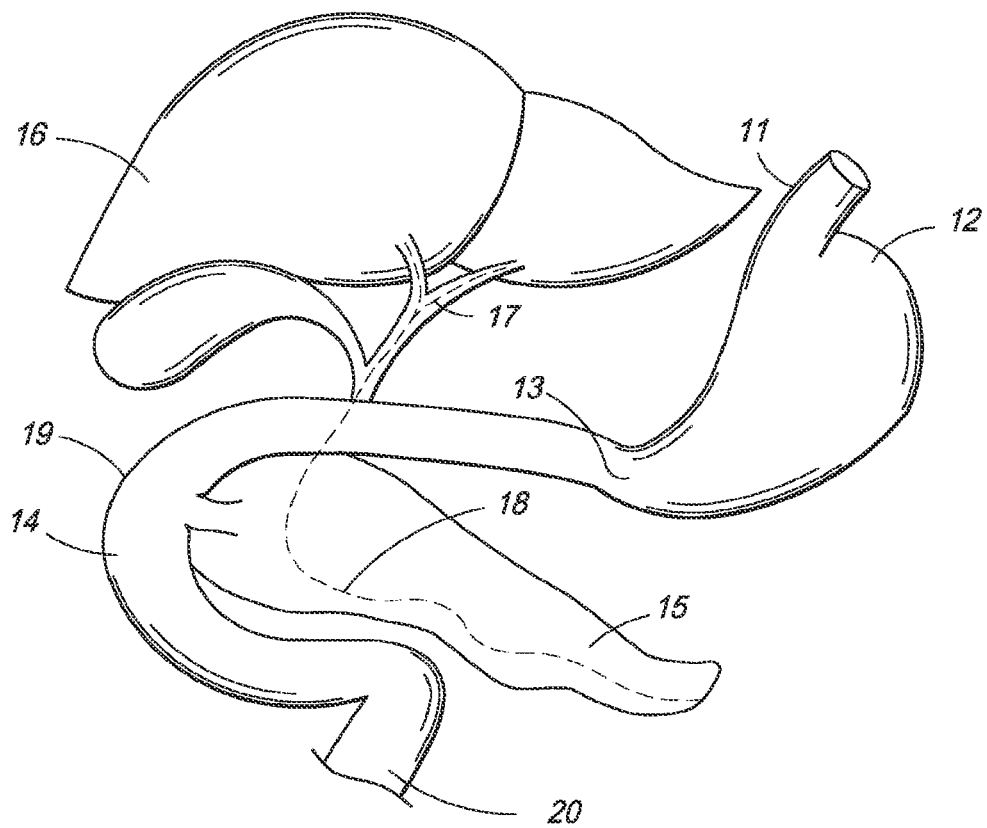
FIG. 1 is an illustration of the upper gastrointestinal system.

In one embodiment, the present invention is directed towards an intragastric device of dynamic weight used in obese patients to induce weight loss. In one embodiment, the intragastric device contains a non-inflatable wire mesh structure, or a spiral structure made of shape memory metal or shape memory polymer that changes from a pre-deployment compressed cylindrical shape to a post-deployment sphere, oval, kidney bean or any predefined shape of significant volume. The device changes back and forth from the pre-deployment to post-deployment shape by minimal mechanical force and/or temperature changes arising from the room temperature pre-deployment shape to the body temperature post-deployment shape. The device is delivered endoscopically to the stomach via a catheter. The device can be placed through the endoscope, over an endoscope or over a guidewire with endoscopic or fluoroscopic guidance/assistance.

The device has a pre-deployment compressed shape to facilitate insertion and post-deployment expanded shape that resides in the gastric lumen. Post-deployment volume of the device is significantly larger than pre-deployment volume. The post-deployment device occupies a significant volume in the stomach, thereby reducing available gastric volume available for storage of ingested food. This restricts the amount of food intake, inducing satiety and curbing one's appetite.

In one embodiment, the wire structure contains differently weighted material to assist in proper positioning within the stomach. In one embodiment, lighter weighted material is positioned at the top of the wire structure proximate to the top openings and heavier weighted material is positioned at the bottom of the structure, proximate to the bottom openings. This differential weighting insures that the device will be properly situated within the stomach to effectuate the intended effect of slower gastric emptying. In addition, the differential weighting provides for proper gastric positioning without the need of physically anchoring the wire mesh structure to the stomach wall. The differential weight property can also be provided by the ingested food material that enters the device and is selectively accumulated toward the bottom of the device facilitated by the gravitational pull. The wire mesh structure is free to move about within the stomach while still maintaining its correct top to bottom alignment facilitated by the gravitational pull.

In one embodiment, the present invention is directed toward a wire mesh or spiral structure with an exterior housing structure that is defined by openings, holes, voids or spaces of varying sizes. The wire mesh or spiral structure has larger spaces or openings within its upper portion and smaller spaces within its bottom portion. The larger or more spaces or openings within the upper portion of the device are preferably aligned with, and directed toward, the esophagus, the cardia, the fundus or the body of the stomach and the fewer or smaller spaces or openings within the bottom portion of the device are preferably aligned with, and directed toward, the gastric antrum or the intestines. These spaces or openings provide two additional benefits beyond the feeling of satiety provided by the expanded second configuration.

First, differential sizes or numbers resulting in differential surface area of the upper and lower openings enable the device to act like a time release capsule. The larger surface area of the openings toward the top two-thirds of the structure permit a larger volume of food to enter into the device, as compared to the volume of food permitted to leave the device via the smaller surface area of the openings that define the bottom of the device, thereby making the device a temporary storage unit with a delayed release of the nutrients. As the stomach grinds solid food into liquid food, or chyme, the chyme passes into and is sequestered inside the intragastric device. The chyme is then slowly released back into the stomach, thereby delaying gastric emptying and inducing satiety. The gastric emptying can also be controlled by varying both the number and size of these openings, holes, spaces or voids to differentially control the inflow and outflow of the food from the device. In essence, the ratio of the surface area of the inflow and the outflow as calculated by the size and the number of inflow and outflow opening controls the rate of emptying from the device and hence the gastric emptying.

An additional embodiment of the device has large holes or opening in the middle and smaller opening in the top and bottom halves, thereby allowing the partially digested food to enter in the middle portion with the option to leave from either the top or the bottom half. In another embodiment the top two-thirds of the device has an opening but the lower one-third of the device has a membrane without any openings than stores the partially digested food in the upright position as a bowl and release the food back through the same openings in the top two thirds of the device when the patient is supine. In addition, liquid foods, such as ice cream, will also be sequestered into the dependent portion of the device and released into the stomach more slowly at a later time.

Second, the varying shape, size and number of the openings or spaces in the wire mesh structure allow the device to store ingested food and undergo meal induced dynamic weight change. The device will have a greater weight during and post feeding resulting in an appropriately timed feeling of fullness or satiety. Heavier intra-gastric devices are associated with more satiety and weight loss however they have more side-effects such as nausea and abdominal pain. Slowly, as the food is released out of the device, the weight of the device will decrease over time and return to its baseline weight. Eventually, the device will have a lower weight during fasting, diminishing the side effects commonly associated with an intragastric device, improving patient tolerance. Conventional water filled intragastric balloons are heavier than air filled balloons resulting in a greater feeling of satiety and weight loss but patients suffer from increased side effects resulting higher intolerance and need for premature removal. Air filled balloons are lighter and therefore more tolerable, but are less effective in inducing satiety and hence weight loss. The present invention improves upon both devices by inducing a greater and more normalized feeling of satiety during feeding and post-feeding stage while reducing side effects during the fasting stage.

In another embodiment, the present invention is directed towards a wire mesh or spiral structure partially encompassed, housed, or otherwise enclosed by a membrane. When expanded into the second configuration, the membrane contains opening, holes, voids, or spaces proximate to the top of the device and holes proximate to the bottom of the device. The openings on the top of the device have larger surface area and are preferably aligned with, and directed toward, the esophagus, cardia, fundus or the body of the stomach and the openings at the bottom of the device have same or less surface area compared to the openings on the top and are preferably aligned with, and directed toward, the antrum or pylorus of the stomach or the small intestines. These openings provide two additional benefits beyond the feeling of satiety provided by the expanded second configuration.

First, the device with differentially sized membrane opening, holes or voids acts as a time release capsule. More food enters into the device from the large surface area of the openings at the top than exits from the smaller surface area of the openings at the bottom, resulting in a device that functions as a temporary storage unit with a delayed release of nutrients. As the stomach grinds solid food into liquid food, or chyme, the chyme is sequestered inside the wire mesh device. The chyme is then slowly released back into the stomach, thereby delaying gastric emptying and inducing satiety. In addition, liquid foods, such as ice cream, will also be sequestered into the dependent portion of the device and released back into the stomach more slowly.

Second, the two sets of openings in the wire mesh structure membrane allow the device to undergo dynamic weight change. The device will have a greater weight during and post feeding resulting in an appropriately timed feeling of fullness or satiety. Slowly, as the food exits the device, the weight of the device will decrease over time. Eventually, the device will have a lower weight during fasting, diminishing the side effects commonly associated with an intragastric device, such as nausea and pain. Conventional water filled intragastric balloons are heavier than air filled balloons resulting in a greater feeling of satiety but patients suffer from increased side effects. Air filled balloons are lighter and therefore more tolerable, but are less effective in inducing satiety. The present invention improves upon both devices by inducing a greater and more normalized feeling of satiety during the feeding and post-feeding stage while reducing the side effects.

In another embodiment, the wire mesh structure has portions that are completely covered by a membrane and some portions that are not, resulting in differential release of food. In one embodiment, the top and bottom of the wire mesh structure are completely covered by the membrane and the middle of the structure has openings in the membrane to allow the passage of food. In another embodiment, the wire mesh structure is 90-99% covered by the membrane, leaving only a small area for food passage, thereby increasing the time for gastric emptying. In another embodiment, the membrane covering the wire mesh structure has a ring of large openings in the upper hemisphere of the structure and a ring of smaller openings in the bottom hemisphere of the structure. In another embodiment, the membrane covering the wire mesh structure has more number of openings in the upper hemisphere of the structure and less number of openings in the bottom hemisphere of the structure. In another embodiment, the membrane covering the wire mesh structure has a greater surface area of openings in the upper hemisphere of the structure and lesser surface area of openings in the bottom hemisphere of the structure. This different configuration also results in delayed gastric emptying and dynamic weight change of the wire mesh structure.

Gastric fundus is involved in the release various gut hormones such as "hunger hormones", ghrelin, orexin and PYY 3-36, and "satiety hormones", e.g., leptin, obestatin, nesfatin-1. The release of these hormones is mediated by contact of gastric mucosa with various nutrients in the ingested food. Further, the membrane of the top portion of the wire mesh structure will prevent sequestered food from coming into contact with the gastric cardia and fundus. This results in physiological exclusion of the gastric cardia and fundus, a mechanism thought to play a role in satiety and weight loss and one of the mechanism in play in RGB gastric bypass surgery.

In another embodiment, layers of membrane act as a flap valve controlling the directionality of the movement of the food in the various portions of the intragastric device. Just like the size of the openings, the size, shape, position and directionality of the valves can be varied to achieve desired gastric emptying effect.

In another embodiment, a sleeve can be attached to the intragastric device, where the sleeve extends from the stomach through the duodenum and into the jejunum. The sleeve functions to transit the sequestered chyme from the wire mesh structure directly to the mid-jejunum. The sleeve therefore acts to bypass portions of the gastrointestinal (GI) tract in order to limit the absorption of specific materials in the intestine. The benefits provided by a sleeve are similar to those provided by Roux-en-Y gastric bypass surgery, namely, weight loss and improvement of type II diabetes. These benefits are accomplished in at least two ways.

First, bypass of the duodenum and proximal duodenum improves type II diabetes by changing the hormone release from the proximal portion of the small intestine. This may also induce weight loss by inhibiting or decreasing the release of pacreatico-biliary secretions and inducing maldigestion and malabsorption. Second, the sleeve acts to release undigested nutrients into the mid-jejunum, improving type II diabetes by changing the hormone release from the mid portion of the small intestine. This may induce weight loss by maldigestion and malabsorption of these nutrients. While conventional sleeve devices may perform certain of these functions, conventional sleeves must be anchored in the GI tract to avoid migration. Anchoring often results in complications, including infection, bleeding, perforation, and, if not anchored correctly, migration of the sleeve leading to possible obstruction and death. In the present invention, the sleeve is physically attached to the intragastric device, where the intragastric device serves as the anchor for the sleeve. This removes the need for the sleeve to be physically anchored to the GI tract, eliminating the associated complications. In addition, the current device offers functional advantages over conventional sleeves by concurrently controlling food and calorie intake, inducing satiety, and controlling gastric emptying, which is not accomplished by traditional sleeve devices.

In another embodiment the intragastric device has multiple opening, holes, voids or spaces in the top half and a membrane with at least one opening, hole, or void in the bottom half where the bottom opening directs the food preferentially into the sleeve device. In this embodiment, the bottom half of the intragastric device acts as a funnel, collecting all the food entering the device through the top half in the bottom half and preferentially releasing it into the sleeve which in turn will deliver the food/nutrients to the mid small intestine thus bypassing the proximal small intestine.

In one embodiment the entire intragastric device is covered by the membrane with opening that have valves throughout the device directing the food into the intragastric device where it get sequestered and is preferentially emptied through the opening in the bottom half of the device into the sleeve and delivering it to the mid small bowel thus bypassing the proximal small intestine. In this embodiment, the intragastric device sequesters the nutrients/food and, through the sleeve attachment, empties them into the mid small intestine.

The above two embodiments mimic Roux-en-Y gastric bypass (RGB) surgery by creating gastric restriction, isolation of gastric fundus and bypassing the proximal small intestine thus resulting in maximum weight loss and control of Type-II diabetes. In addition the device has ability to regulate gastric emptying in a manner that cannot be traditionally achieved by RGB gastric bypass surgery. The controlled and prolonged release of nutrients into the mid and distal small bowel will result in prolonged satiety via modulation of release of gut hormones such as "hunger hormones", ghrelin, orexin, and PYY 3-36, and "satiety hormones", e.g., leptin, obestatin, and nesfatin-1.

In one embodiment, a second intragastric device can be attached to an already deployed intragastric device, thereby increasing the volume occupied in the stomach. This serves to further limit the amount of food ingested by a patient and also further delays gastric emptying as food flows from one intragastric device into the other before releasing back into the stomach or into the attached sleeve device. This allows for tailoring the therapy to a specific patient's need by increasing or decreasing the volume of the intragastric devices. In addition, this allows for the possibility of stepwise increases or decreases in the device based therapy based on therapeutic response and side-effect profile. This is usually performed in the inflatable intragastric devices by instilling or removing fluids. However, such devices do not have the ability to regulate gastric emptying.

Another part of this invention is a removal device used to remove the intragastric device. The removal device is a catheter inserted per-orally or via an endoscope and passed through a proximal and optionally through a distal opening of the intragastric device. The catheter then engages and secures the proximal and distal end of the expanded intragastric device and the device is then constrained back into its pre-deployed shape using mechanical force. The reversion to its pre-deployed state in a shape memory device can be further facilitated by instillation of cold fluid into the intragastric device, lowering the temperature of the intragastric device.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is an illustration of the upper gastrointestinal system. After swallowing, food passes rapidly through the esophagus 11 into the stomach 12. There, it is digested for a period of time and undergoes the process of dilution to an iso-osmotic concentration by grinding and mixing with gastric juices. The stomach 12 relaxes to accommodate the volume of ingested food. As the stomach 12 gets filled with food the sensation of fullness or satiety is generated by stretch receptors in the gastric wall and the person stops eating. The iso-osmotic food, known as chyme, then passes through the pylorus 13 into the duodenum 14. Passage of chyme into the duodenum 14 results in the release of enzyme rich pancreatic secretions from the pancreas 15 and bile salt rich biliary secretions from the liver 16. The biliary secretions travel through the common bile duct 17 where they combine with the pancreatic secretions arriving through the pancreatic duct 18 to form the ampulla of vater 19. The ampulla of vater 19 serves as the entry point for the secretions to be deposited into the duodenum 14. In the jejunum 20, the mixing of pancreatic and biliary secretions with the chyme results in the digestion of proteins, fats, and carbohydrates, which are then absorbed into the blood stream.

Figure 2:
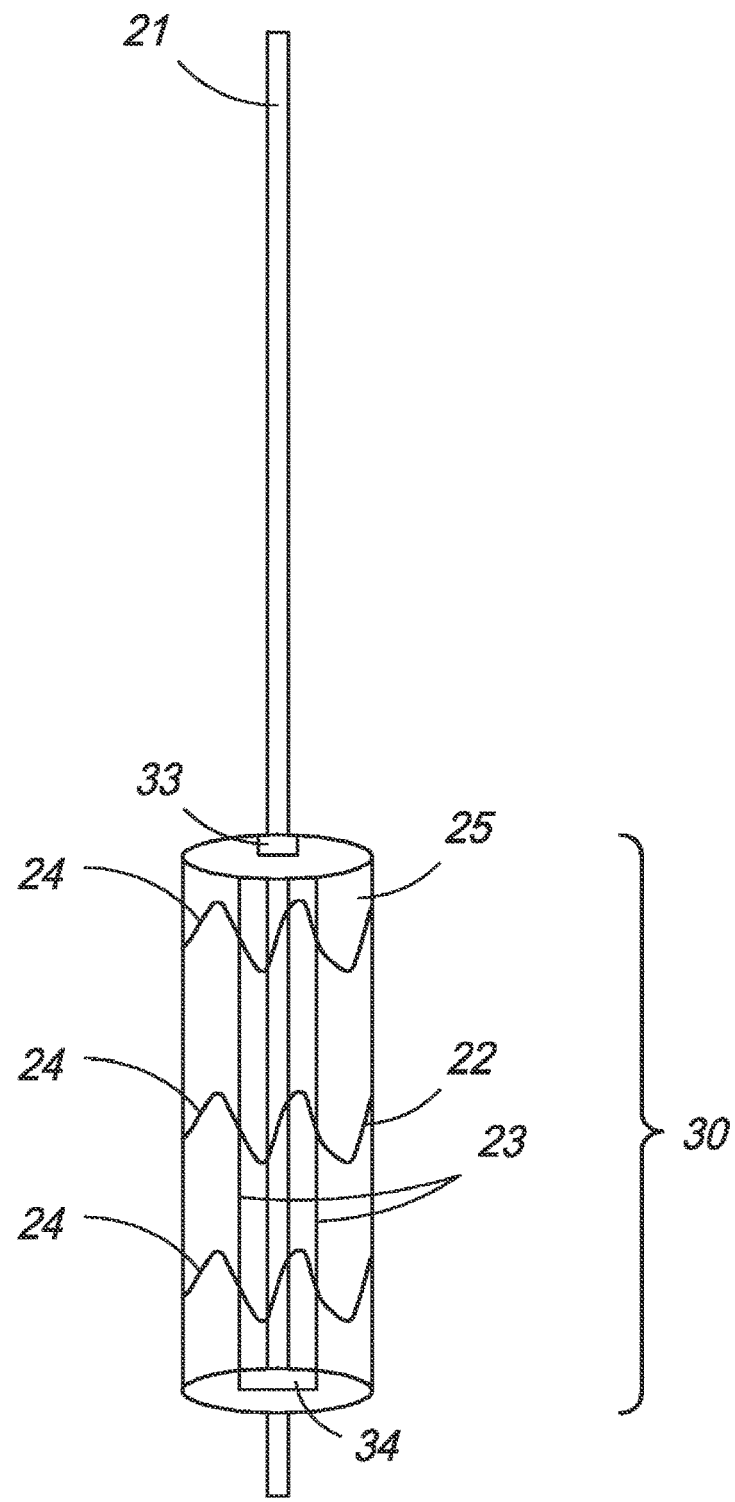
FIG. 2 is an illustration of one embodiment of the intragastric device in an exemplary pre-deployment configuration.

FIG. 2 is an illustration of one embodiment of the intragastric device 30 in the pre-deployment configuration. A catheter 21 holds the compressed wire mesh structure 22. The compressed wire mesh device is held in place by either a constraining catheter, sheath, or a silk suture or thread. The compressed wire mesh structure 22 is made of vertical elements 23 and horizontal elements 24. Optionally the intragastric device can be a metal spiral that is cylindrical, comparable to a spring, in constrained positioned and a spiral metal sphere in the deployed shape. In one embodiment, the vertical elements 23 and horizontal elements 24 comprise a metal. In another embodiment, the vertical elements 23 and horizontal elements 24 comprise an alloy. In another embodiment, the vertical elements 23 and horizontal elements 24 comprise a polymer. In yet another embodiment, the vertical elements 23 and horizontal elements 24 comprise a shape memory metal. In yet another embodiment, the vertical elements 23 and horizontal elements 24 comprise a shape memory alloy. In yet another embodiment, the vertical elements 23 and horizontal elements 24 comprise a shape memory polymer. In one embodiment, a weight 34 is positioned proximate to the bottom of the intragastric device. The weight serves to keep the intragastric device in the proper alignment when positioned in the stomach. Preferably, the weight is in a range of 1 to 500 grams, preferably between 10 and 50 grams. The catheter 21 has optional ports for passage of wire, contrast or an endoscope located in the center of the catheter shaft. One of ordinary skill in the art would appreciate the structure and configuration of a compressed structure within a catheter that, after removing a constraining sheath, is permitted to expand at a treatment location.

Figure 3:
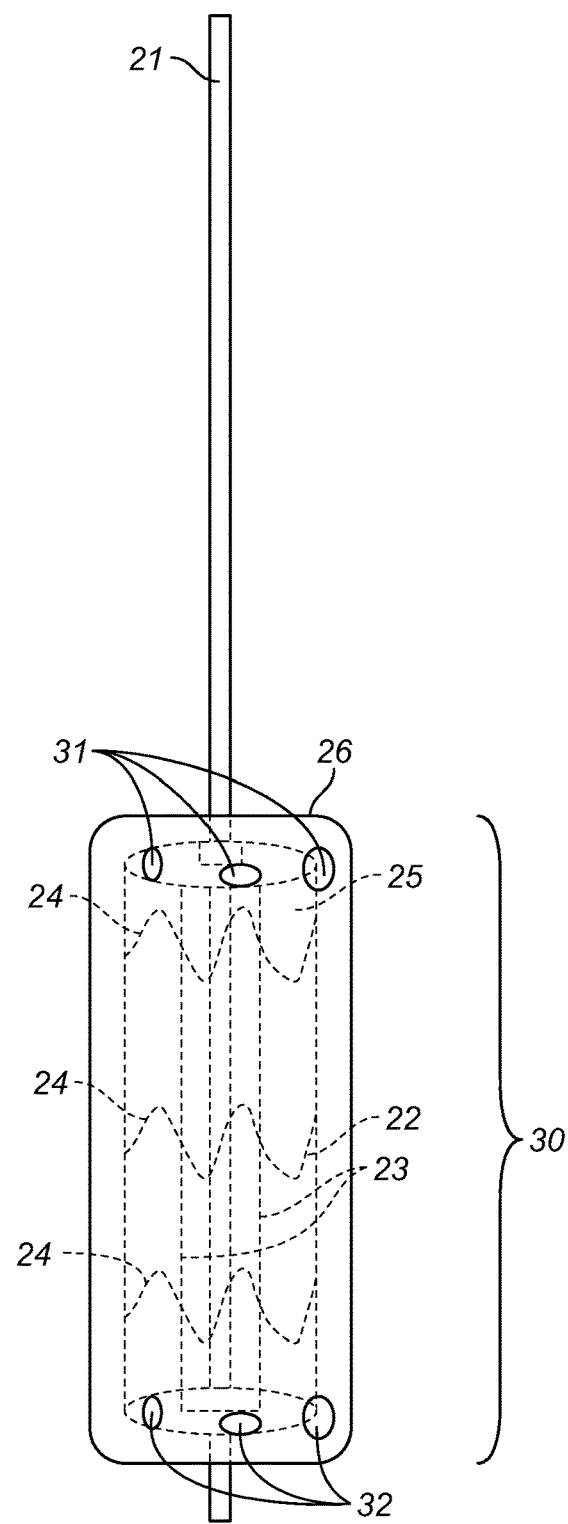
FIG. 3 is an illustration of another embodiment of the intragastric device in an exemplary pre-deployment configuration.

FIG. 3 is an illustration of another embodiment of the intragastric device 30 in the pre-deployment configuration. A catheter 21 holds the compressed wire mesh structure 22. The compressed wire mesh structure 22 is made of vertical elements 23 and horizontal elements 24. In one embodiment, the vertical elements 23 and horizontal elements 24 comprise metal. In another embodiment, the vertical elements 23 and horizontal elements 24 comprise an alloy. In another embodiment, the vertical elements 23 and horizontal elements 24 comprise a polymer. In yet another embodiment, the vertical elements 23 and horizontal elements 24 comprise a shape memory metal. In yet another embodiment, the vertical elements 23 and horizontal elements 24 comprise a shape memory alloy. In yet another embodiment, the vertical elements 23 and horizontal elements 24 comprise a shape memory polymer. In one embodiment, the compressed wire mesh structure 22 is partially enveloped by a membrane 26. The membrane 26 is made up of a digestive resistance material.

In one embodiment, the membrane 26 comprises latex. In another embodiment, the membrane 26 comprises parylene. In another embodiment, the membrane 26 comprises polyurethane. In another embodiment, the membrane 26 comprises polytetrafluoroethylene (PTFE). In another embodiment, the membrane 26 comprises fluorinated ethylene-propylene. In another embodiment, the membrane 26 comprises Dacron. In yet another embodiment, the membrane 26 comprises polyethylene terephthalate (PET). In one embodiment, the membrane 26 comprises openings 31 with larger surface area proximate the top of the intragastric device 30 for receiving chyme and openings 32 with a smaller surface area proximate the bottom of the intragastric device 30 for slow release of the sequestered chyme.

Figure 4:
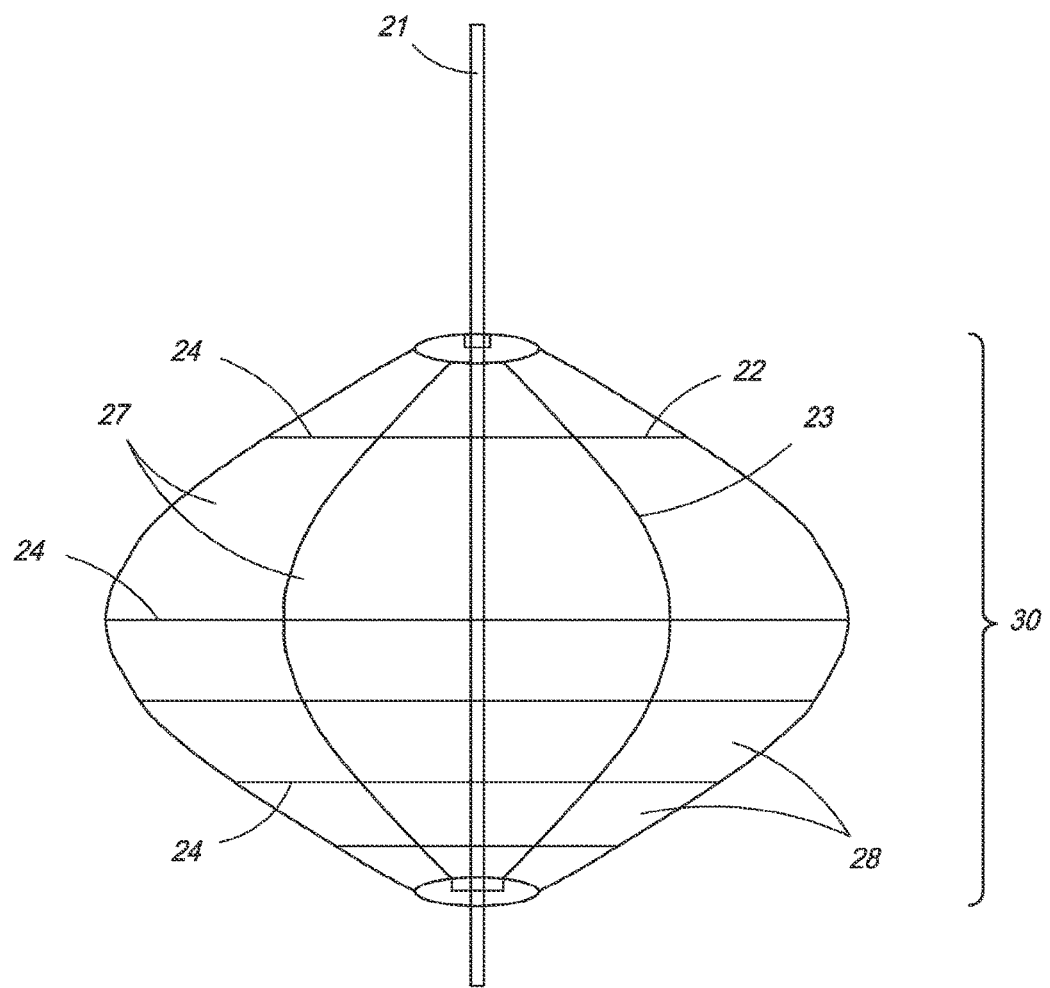
FIG. 4 is an illustration of one embodiment of the intragastric device in an exemplary post-deployment configuration.

FIG. 4 is an illustration of one embodiment of the intragastric device 30 in the post-deployment configuration. The catheter 21 is positioned into the stomach and the compressed wire mesh structure 22 is released. After deployment, the wire mesh structure 22 assumes its expanded configuration. This is achieved through the use of shape memory technology as the vertical elements 23 and horizontal elements 24 expand to assume their pre-defined, post-deployment shapes. The expansion of the vertical elements 23 and horizontal elements 24 creates the spaces 27 with larger surface area proximate the top of the intragastric device 30 and the spaces 28 with similar or smaller surface area proximate the bottom of the intragastric device 30. These differing sized spaces slow gastric emptying and induce a longer period of satiety.

The spaces within the structure can range in size between 1 μm and 10 cm, preferably between 1 mm and 5 cm and most preferably between 5 mm and 10 mm. The spaces at the top of the structure can be same size as the spaces at the bottom of the structure. Alternatively, spaces at the bottom of the structure are smaller but no smaller than 50% of the larger openings at the top of the structure, otherwise food will accumulate in the device and interfere with its functionality. In one embodiment, the gastric emptying is achieved by having each opening at the top have the same surface area as each opening at the bottom. In this embodiment, the number of openings at the bottom of the structure will be less than the number of openings at the top of the structure. If one wished to delay gastric emptying by 50%, the number of openings in the bottom will be approximately 50% of the number of the openings in the top of the structure. Alternatively, the openings at the top can have a larger surface area than the openings at the bottom and, if one wished to delay gastric emptying by 50%, the total surface area of the openings in the bottom will be approximately 50% of the total surface area of the openings in the top of the structure.

After deployment, the catheter 21 is removed, leaving the deployed intragastric device 30 in the stomach. The post-deployment intragastric device 30 occupies the gastric lumen thereby decreasing the effective volume available to accommodate ingested food. The post-deployment intragastric device 30 presses upon the gastric wall, stimulating the stretch receptors and inducing the sensation of fullness or satiety. A sphere is the most effective embodiment of the device as it has the most volume for a given pre-deployment length and surface area.

In various possible embodiments, the pre and post-deployment configurations of the intragastric device contain the following attributes:

| Pre-deployment length (cm) | Post-deployment radius (cm) | Post-deployment volume (cc) |
|---|---|---|
| 6 | 1.9 | 29 |
| 9 | 2.9 | 98 |
| 12 | 3.8 | 233 |
| 15 | 4.8 | 456 |
| 18 | 5.7 | 787 |
| 20 | 6.4 | 1080 |
| 25 | 8.0 | 2109 |
| 30 | 9.5 | 3645 |
| 40 | 12.7 | 8639 |
| 50 | 15.9 | 16873 |

The post-deployment radius (r) is equal to pre-deployment length (l) divided by pi ($\pi$) and the post-deployment volume (v) is equal to $4 l3/3\pi2$.

Figure 5:
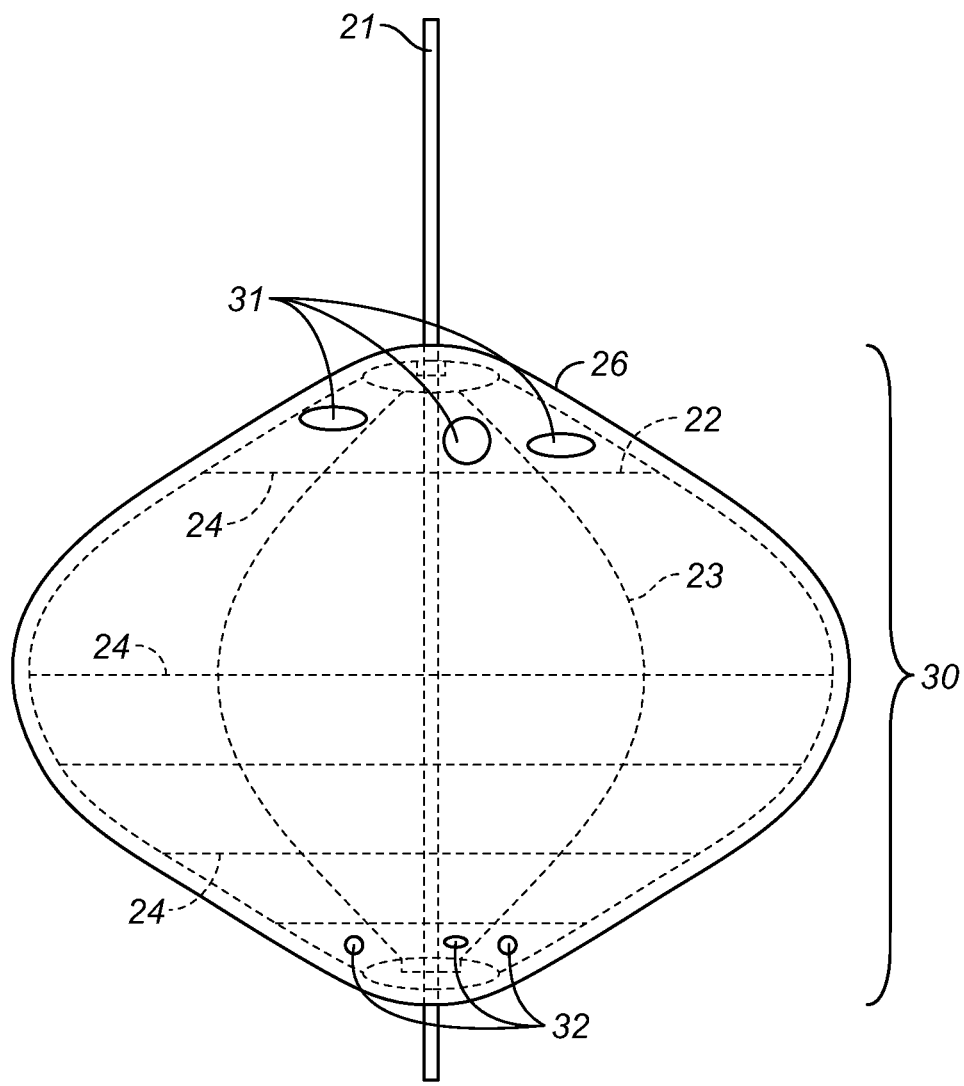
FIG. 5 is an illustration of another embodiment of the intragastric device in an exemplary post-deployment configuration.

FIG. 5 is an illustration of another embodiment of the intragastric device 30 in the post-deployment configuration. The catheter 21 is positioned into the stomach and the compressed wire mesh structure 22 is released. After deployment, the wire mesh structure 22 assumes its expanded configuration. This is achieved through the use of shape memory technology as the vertical elements 23 and horizontal elements 24 expand to assume their pre-defined, post-deployment shapes. The enveloping membrane 26 gives the intragastric device the quality of being partially permeable to gastric fluids. Large holes 31 are positioned proximate the top of the intragastric device 30 and small holes 32 are positioned proximate the bottom of the intragastric device 30. These differing sized holes in the membrane 26 allow for slowing of gastric emptying. After deployment, the catheter 21 is removed, leaving the deployed intragastric device 30 in the stomach. The post-deployment intragastric device 30 occupies the gastric lumen thereby decreasing the effective volume available to accommodate ingested food. The post-deployment intragastric device 30 presses upon the gastric wall, stimulating the stretch receptors and inducing the sensation of fullness or satiety.

FIG. 5A is an illustration of another embodiment of the intragastric device 30 in an exemplary pre-deployment configuration. The pre-deployment configuration takes a compressed, cylindrical shape to facilitate insertion.

FIG. 5B is an illustration of the intragastric device 30 of FIG. 5A in an exemplary post-deployment configuration. The post-deployment configuration takes an expanded, spiral shape to occupy gastric volume and permit the sequestering of food within the device. In one embodiment, the spiral structure is covered with a membrane 35 containing openings of same or different sizes. In one embodiment, the openings have valves to direct the flow of food preferentially in an inward or an outward direction.

Figure 5D:
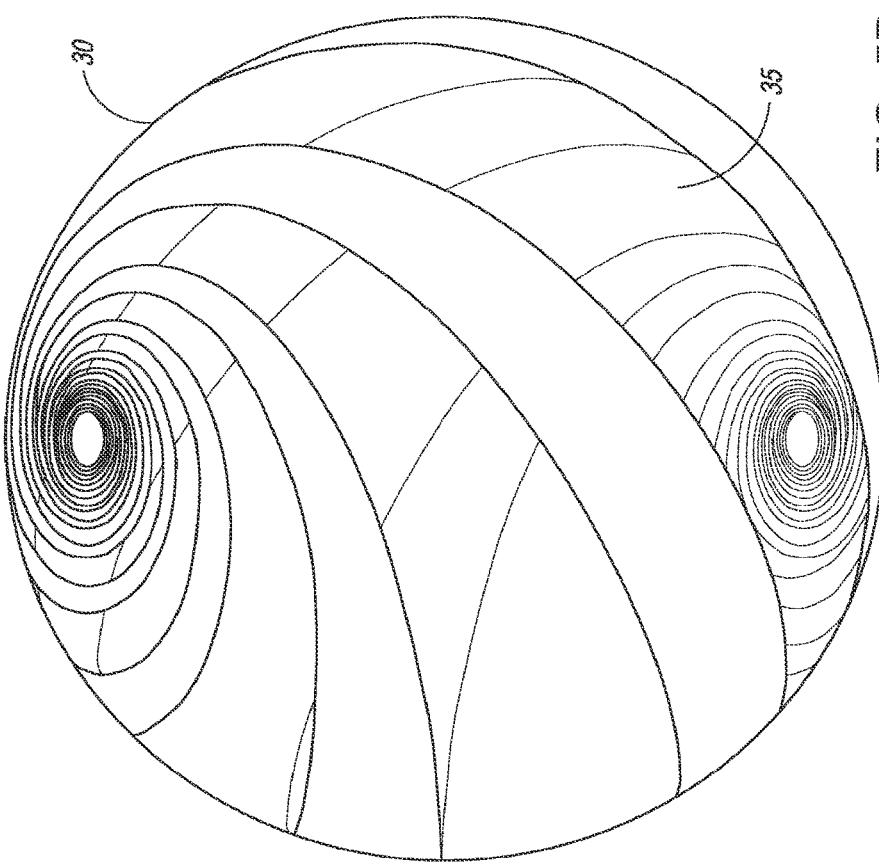
FIG. 5D is an illustration of the intragastric device of FIG. 5C in an exemplary post-deployment configuration.
Figure 5C:
FIG. 5C is an illustration of yet another embodiment of the intragastric device in an exemplary pre-deployment configuration.

FIG. 5C is an illustration of yet another embodiment of the intragastric device 30 in an exemplary pre-deployment configuration. The pre-deployment configuration takes a compressed, cylindrical shape to facilitate insertion.

FIG. 5D is an illustration of the intragastric device 30 of FIG. 5C in an exemplary post-deployment configuration. The post-deployment configuration takes an expanded, spiral shape to occupy gastric volume and permit the sequestering of food within the device. In one embodiment, the spiral structure is covered with a membrane 35 containing openings of same or different sizes. In one embodiment, the openings have valves to direct the flow of food preferentially in an inward or an outward direction.

FIG. 5E is an illustration of yet another embodiment of the intragastric device 30 in an exemplary pre-deployment configuration. The pre-deployment configuration takes a compressed, cylindrical shape to facilitate insertion.

FIG. 5F is an illustration of the intragastric device 30 of FIG. 5C in an exemplary post-deployment configuration. The post-deployment configuration takes an expanded, wire mesh shape to occupy gastric volume and permit the sequestering of food within the device. In one embodiment, the wire mesh structure is covered with a membrane 35 containing openings of same or different sizes. In one embodiment, the openings have valves to direct the flow of food preferentially in an inward or an outward direction.

Figure 5G:
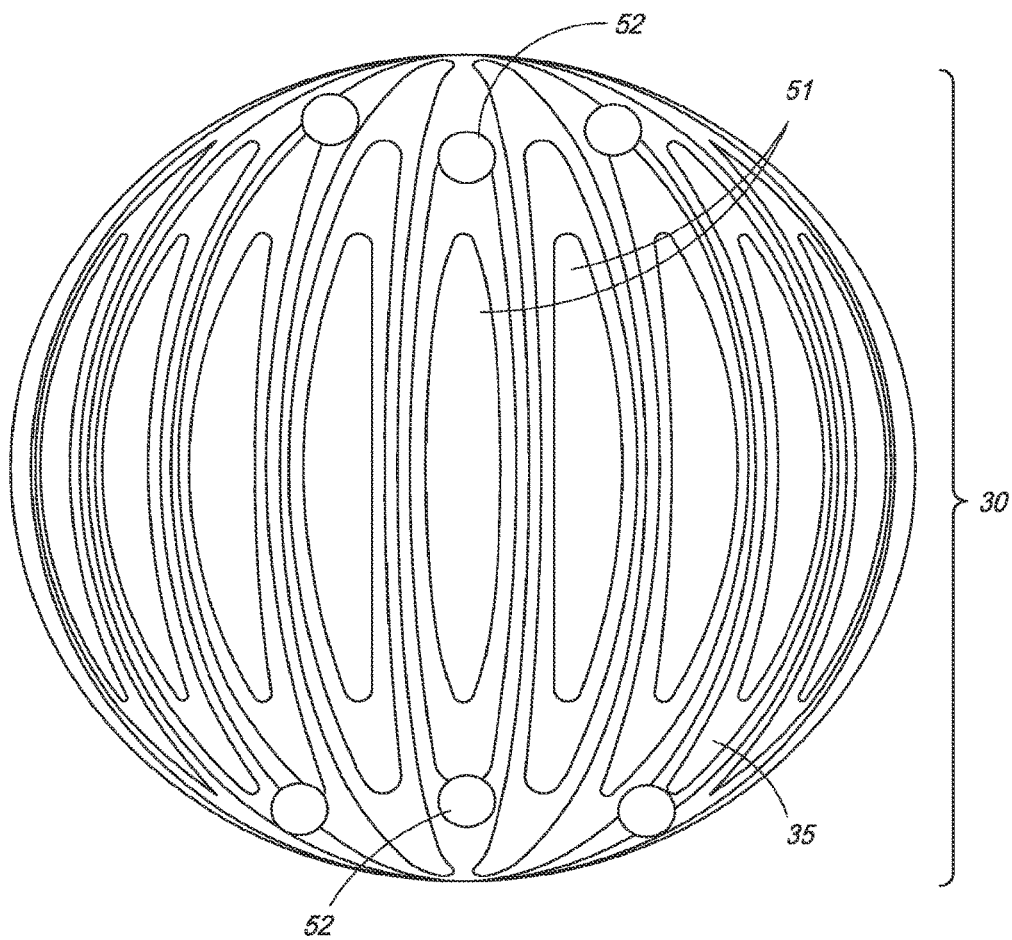
FIG. 5G is an illustration of one embodiment depicting an exemplary post-deployment membrane covered intragastric device with varying sized holes along its surface.

FIG. 5G is an illustration of one embodiment depicting an exemplary post-deployment, membrane 35 covered intragastric device 30 with varying sized openings along its surface. The middle two-thirds of the device 30 contain larger holes 51 and the top and bottom one-third contain smaller holes 52. In one embodiment, the larger holes 51 have valves composed of the same membranous material to direct the flow of food preferentially into the device 30. Thereafter, food slowly exits the device 30 through the smaller holes 52 positioned at the top and bottom of the device 30, thereby delaying gastric emptying.

FIG. 6 is an illustration of one embodiment depicting a possible configuration of the intragastric device 30 post-deployment. In this embodiment, the intragastric device takes the shape of a sphere.

FIG. 6A is an illustration of one embodiment depicting another possible configuration of the intragastric device 30 post-deployment. In this embodiment, the intragastric device 30 takes the shape of a kidney bean.

FIG. 6B is an illustration of one embodiment depicting another possible configuration of the intragastric device 30 post-deployment. In this embodiment, the intragastric device 30 takes the shape of an oval.

FIG. 6C is an illustration of one embodiment depicting another possible configuration of the intragastric device 30 post-deployment. In this embodiment, the intragastric device 30 takes the shape of a boot, with the lower, toe shaped portion positioned proximate to the pylorus.

FIG. 6D is an illustration of one embodiment depicting another possible configuration of the intragastric device 30 post-deployment. In this embodiment, the intragastric device 30 takes the shape of an inverted egg.

FIG. 7 is an illustration of the intragastric device 30 being deployed in the stomach 12. The catheter 21 used to deliver the intragastric device 30 is depicted as it traverses the esophagus 11. The partially deployed device 30 is shown in the stomach 12.

FIG. 8 is an illustration of the fully deployed intragastric device 30 in the stomach 12. The intragastric device 30 occupies a significant portion of the stomach 12, thereby limiting the available volume to accommodate ingested food. The catheter used for delivery has been removed.

FIG. 9 is an illustration of the intragastric device 30 with an attached sleeve 40. The top end of the sleeve 40 is attached to the bottom of the intragastric device 30. The top end of the sleeve 40 completely covers, encases, or otherwise envelopes the bottom holes 32 of the intragastric device 30 so that all chyme released from the intragastric device 30 will enter only into the sleeve 40. A second sleeve 41 is attached to the intragastric device 30 using wires, sutures or strings 45 and the opening 46 of this sleeve resides in the proximal duodenum to capture any food that does not enter the intragastric device 30 but passes alongside the intragastric device through the pylorus into the duodenum.

Figure 9A:
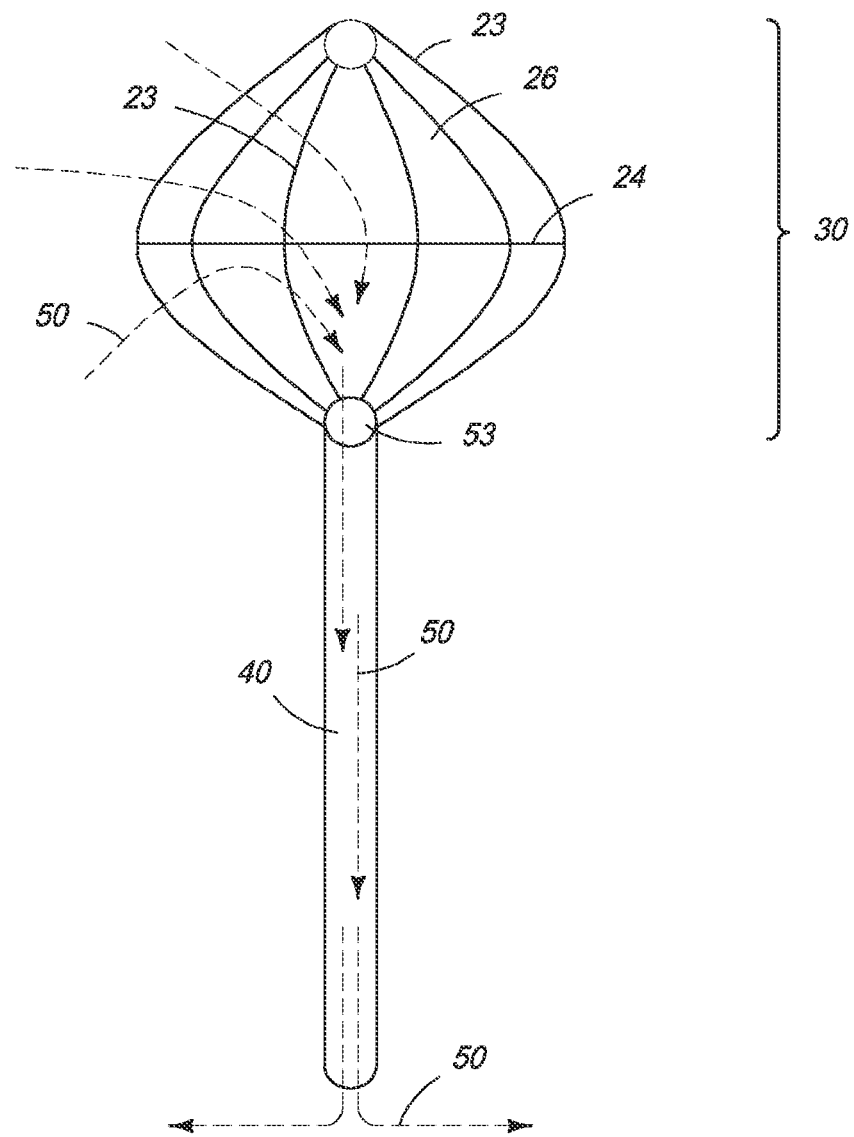
FIG. 9A is an illustration of one embodiment of an intragastric device with an attached sleeve in an exemplary post-deployment configuration.

FIG. 9A is an illustration of one embodiment of an intragastric device 30 with an attached sleeve 40 in an exemplary post-deployment configuration. The vertical members 23 and horizontal members 24 of the wire mesh structure are depicted in their expanded post-deployment configuration. In one embodiment, the device 30 is covered by a membrane 26 containing openings to permit entry of food into the device 30. In one embodiment, the openings have valves to direct the flow of food into the device 30. Once the device is fully deployed into a patient's upper gastrointestinal tract, food 50 passes into the device 30 through the openings located in the membrane 26. The food 50 is sequestered in the device 30 and slowly exits through the bottom of the device 30 through the opening 53 and into an attached sleeve 40. The food 50 travels along the length of the sleeve 40 and is deposited directly into the jejunum, completely bypassing the pylorus, duodenum, and ampulla of vater.

FIG. 9B is an illustration of another embodiment of the intragastric device 30 with an attached sleeve 40 in an exemplary pre-deployment configuration. The pre-deployment configuration takes a compressed, cylindrical shape to facilitate insertion.

FIG. 9C is an illustration of the intragastric device 30 with an attached sleeve 40 of FIG. 9B in an exemplary post-deployment configuration. The post-deployment configuration takes an expanded, honeycomb shape to occupy gastric volume and permit the sequestering of food within the device. In one embodiment, the honeycomb shaped device is covered with a membrane containing openings of the same or different sizes. In one embodiment, the openings have valves composed of the same membranous material to direct the flow of food preferentially into the device. In one embodiment, the device 30 contains one large opening 53 at the bottom that is wholly covered by the attached sleeve 40. The opening 53 at the bottom of the device 30 allows for the preferential passage of food into the sleeve 40 which in turn delivers the food into the jejunum.

Figure 10:
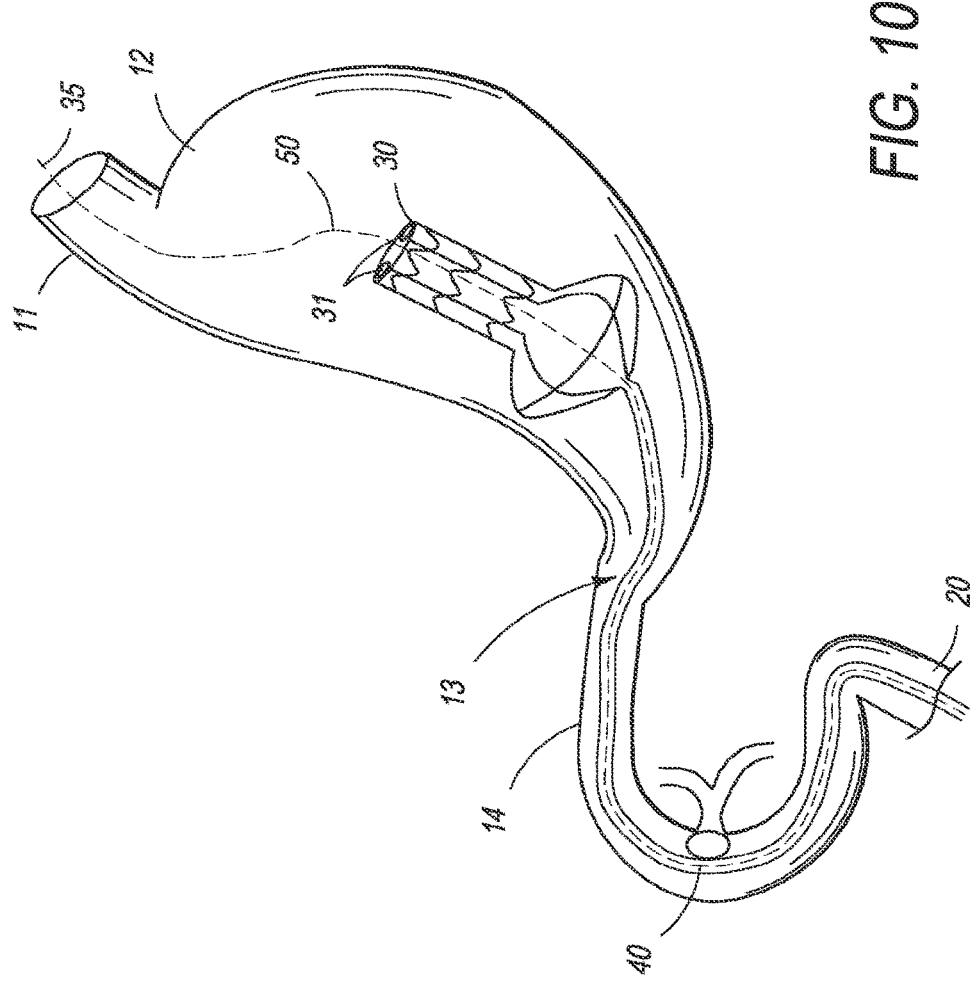
FIG. 10 is an illustration of one embodiment of an intragastric device with an attached sleeve being deployed in the upper gastrointestinal tract.

FIG. 10 is an illustration of the intragastric device 30 with an attached sleeve 40 being deployed over a guidewire 35 in the gastrointestinal tract. The intragastric device 30 is depicted in the stomach 12. The attached sleeve 40 is depicted traveling through the bottom portion of the stomach 12, passing through the pylorus 13 and duodenum 14, and ending and opening up into the jejunum 20. Food 50 passes through the esophagus 11 and into the stomach 12. There it enters the intragastric device 30 through the holes 31 proximate to the top of the intragastric device 30. The food 50 then travels from the intragastric device 30 through the sleeve 40 and into the middle portion of the jejunum 20 without being exposed to the duodenum 14 and proximal jejunum 20.

Figure 11:
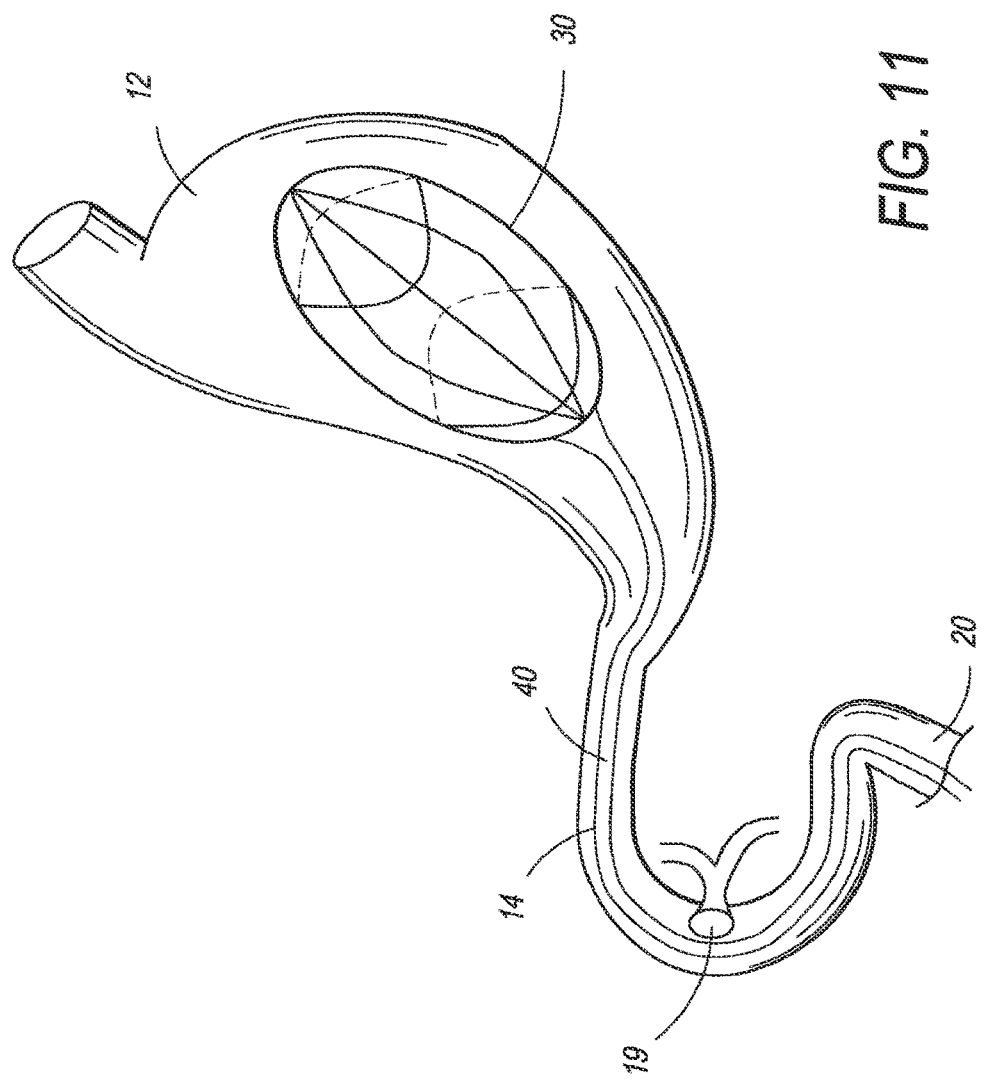
FIG. 11 is an illustration of one embodiment of a fully deployed intragastric device with an attached sleeve in the upper gastrointestinal tract.

FIG. 11 is an illustration of the fully deployed intragastric device with an attached sleeve 40 in the gastrointestinal tract. The intragastric device 30 occupies a significant portion of the stomach 12, thereby limiting the available volume to accommodate ingested food. The sleeve 40 is depicted traveling through the duodenum 14 and into the jejunum 20, bypassing the duodenum 14 and ampulla of vater 19.

Figure 12:
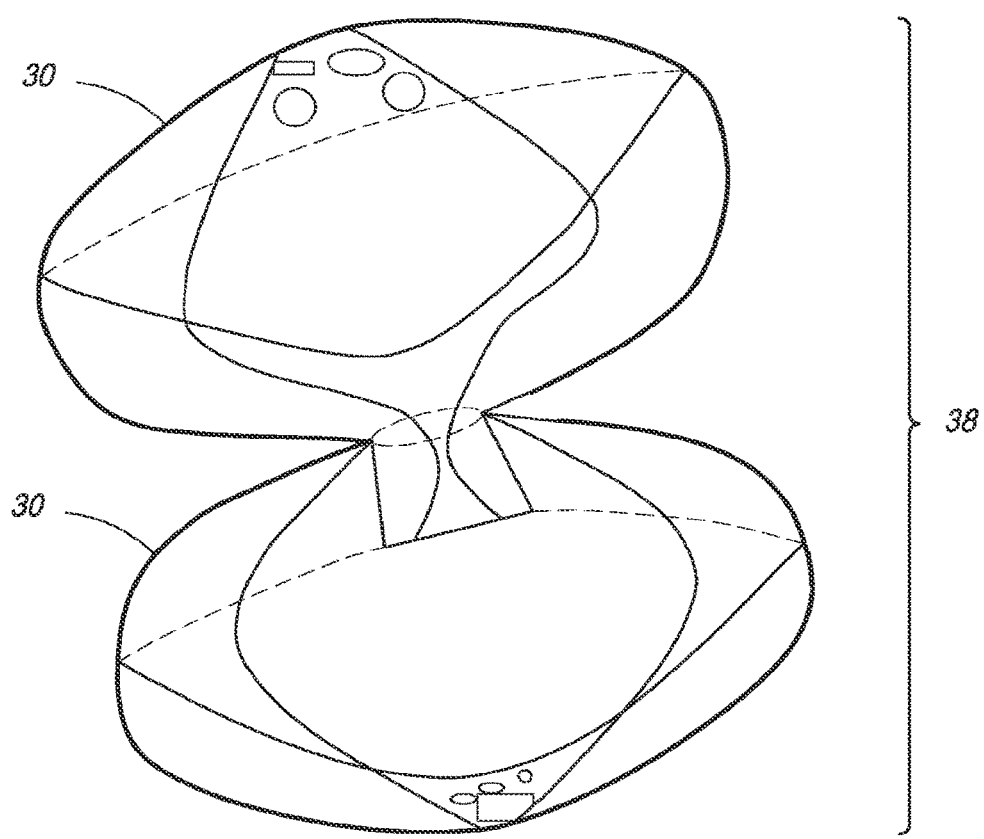
FIG. 12 is an illustration of two single exemplary intragastric devices linked together to form a combined intragastric device.

FIG. 12 is an illustration of two single intragastric devices 30 linked together to form a combined intragastric device 38. The combined intragastric device 38 occupies a greater volume than one single intragastric device 30, thereby inducing satiety even more quickly. The two single intragastric devices 30 are connected, one on top of the other, in such a fashion that food first passes through the large holes 31 in the top of the combined intragastric device 38 and is sequestered in the top single intragastric device 30. The food then slowly passes into, and is sequestered in the bottom of, the single intragastric device 30. Finally, the food slowly releases through the small holes 32 in the bottom of the combined intragastric structure 38 back into the stomach. This double intragastric device configuration acts to further delay gastric emptying, prolonging the sensation of satiety in the patient.

FIG. 13 is an illustration of one single intragastric device 30 being passed over a guidewire 35 and attached to a previously deployed single intragastric device 30 in the stomach 12. The catheter 21 is depicted passing through the esophagus 11 and into the stomach 12. The catheter 21 is deploying the second single intragastric device 30 and assisting in its attachment to the previously deployed intragastric device 30. Operationally, the catheter will be passed into an opening of the existing intragastric device, preferably the opening used by the original catheter to deploy the device. The second device is then deployed with a portion of the second device, such as a neck, protrusion, or other member, fixedly attached to the first device, thereby anchoring the two devices together.

FIG. 14 is an illustration of a fully deployed combined intragastric device 38 in the stomach 12. The two single intragastric devices 30 are depicted attached one on top of the other, occupying a greater stomach 12 volume than one single intragastric device 30.

Figure 15A:
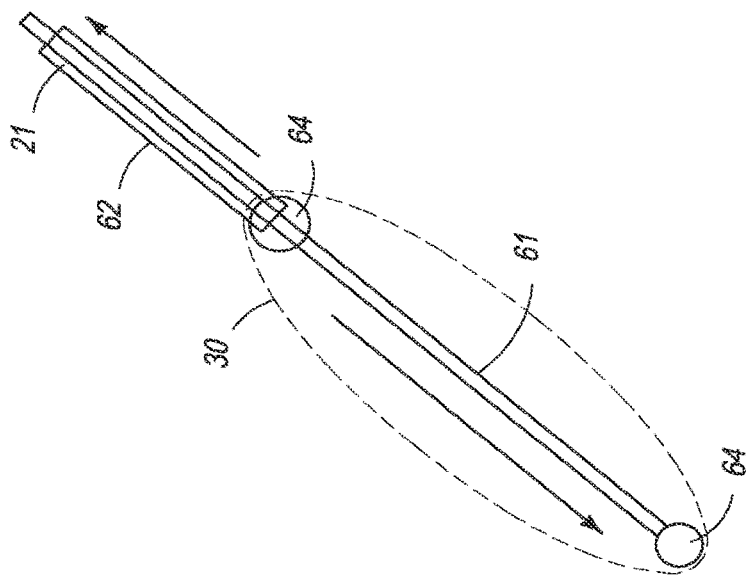
FIG. 15A is an illustration of a gastric device removal catheter attached to an intragastric device in an exemplary pre-deployment configuration.
Figure 15:
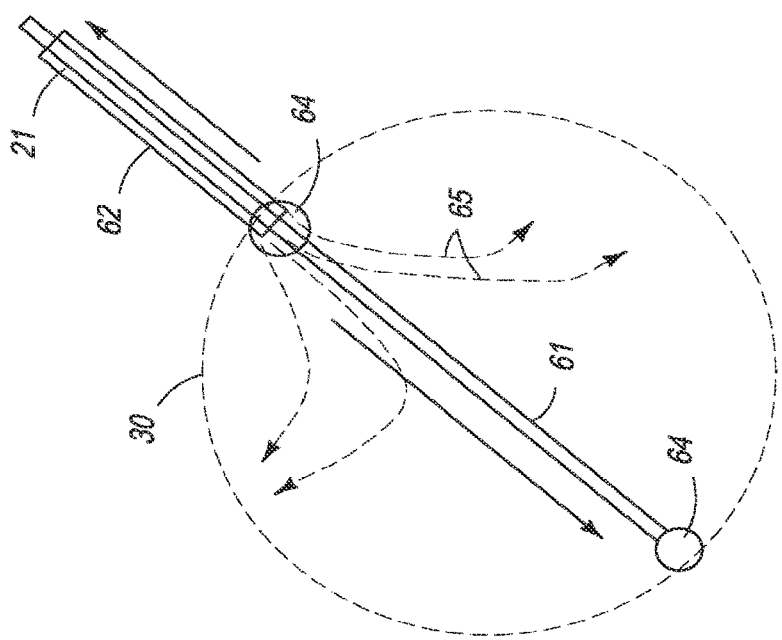
FIG. 15 is an illustration of a gastric device removal catheter attached to an intragastric device in an exemplary post-deployment configuration.

FIG. 15 is an illustration of a gastric device removal catheter 21 attached to an intragastric device 30 in an exemplary post-deployment configuration. The intragastric device 30 is depicted in its expanded, spherical shape. A coaxial catheter 21 is passed through the openings in the gastric device 30 and the walls of the device 30 are engaged by the expanded ends 64 of the catheter 21. The inner catheter 61 and outer catheter 62 are moved in opposite directions resulting in mechanical constriction of the device 30 to its predominantly linear pre-deployment configuration. In one embodiment, cold fluid 65 is instilled into the device 30 via the catheter 21 to lower the temperature of the shape memory structure and assist in further constriction of the device 30 to its predominantly linear pre-deployment structure.

FIG. 15A is an illustration of a gastric device removal catheter 21 attached to an intragastric device 30 in an exemplary pre-deployment configuration. The intragastric device 30 is depicted in its constricted, linear shape after constriction of the shape memory structure via use of the attached gastric device removal catheter 21. The expanded ends 64 of the catheter are depicted engaged with the ends of the linear intragastric device 30. The inner catheter 61 and outer catheter 62 are depicted after having moved opposite one another in order to constrict the intragastric device 30. The constricted, linear pre-deployment configuration facilitates in the removal of the device 30 from a patient's gastric cavity.

FIG. 16 is an illustration of the intragastric device 30 being removed from the stomach 12. The catheter 21 is inserted through the esophagus 11 and attaches to the intragastric device 30 in the stomach 12. The catheter 21 is then used to introduce cold fluid into the intragastric device to lower the temperature of the intragastric device 30, causing the intragastric device 30 to return its shape back to its pre-deployment configuration. Additional mechanical force can be used to constrain the intragastric device 30. Once returned to its initial compressed cylindrical shape, the intragastric device 30 can be removed using the attached catheter 21.

Figure 17B:
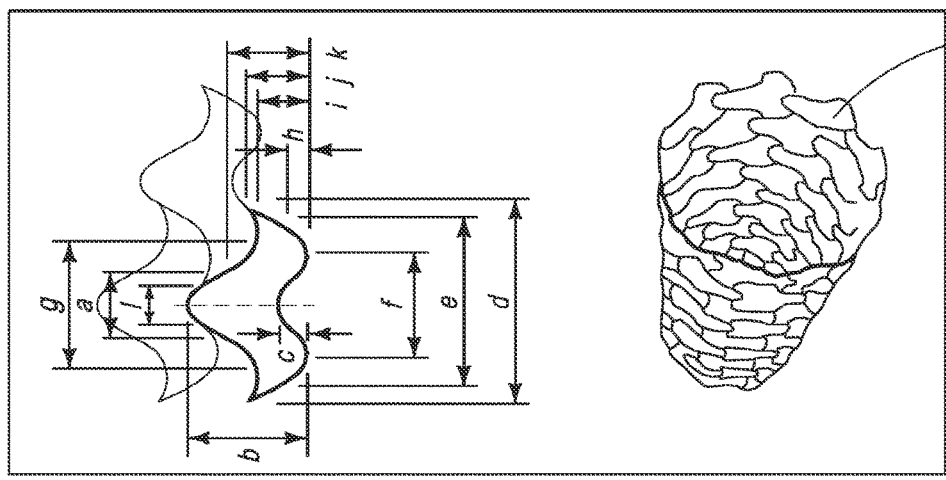
FIG. 17B is an illustration of one embodiment depicting a third exemplary configuration of the wire mesh structure.
Figure 17A:
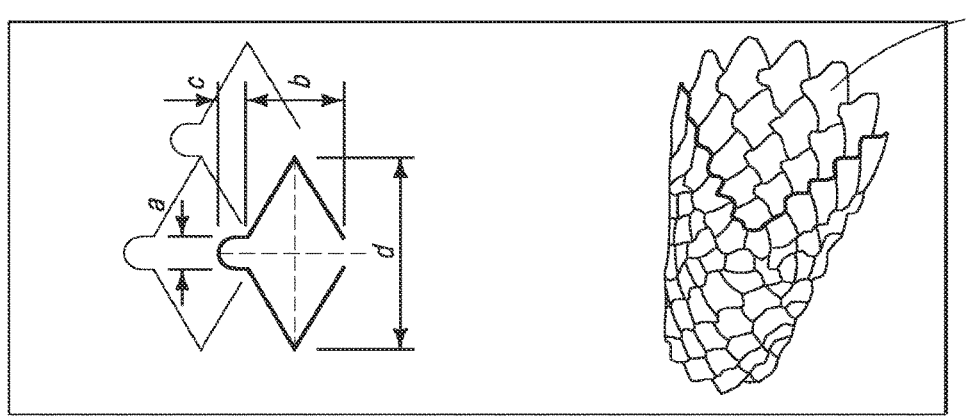
FIG. 17A is an illustration of one embodiment depicting a second exemplary configuration of the wire mesh structure.
Figure 17:
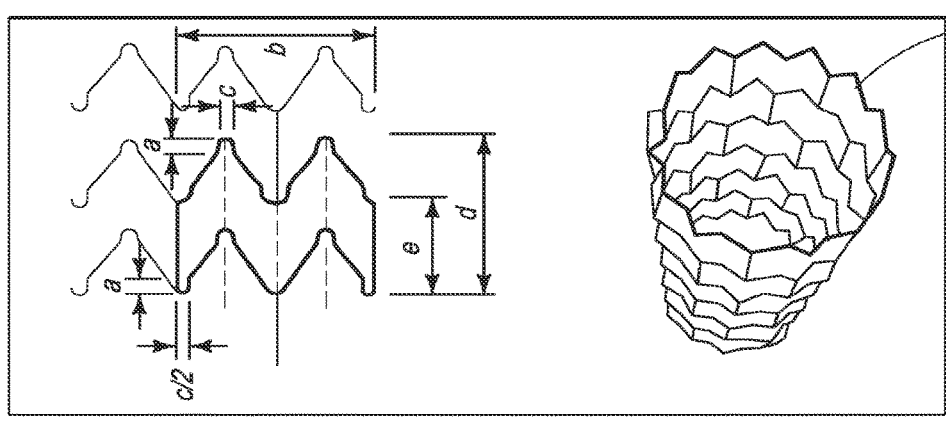
FIG. 17 is an illustration of one embodiment depicting a first exemplary configuration of the wire mesh structure.
Figure 17C:
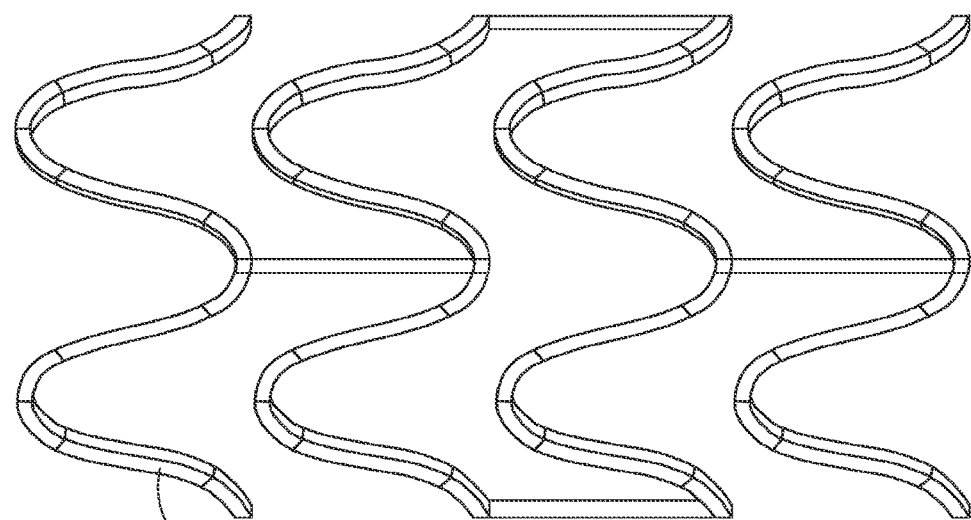
FIG. 17C is an illustration of one embodiment depicting a fourth exemplary configuration of the wire mesh structure.
Figure 17D:
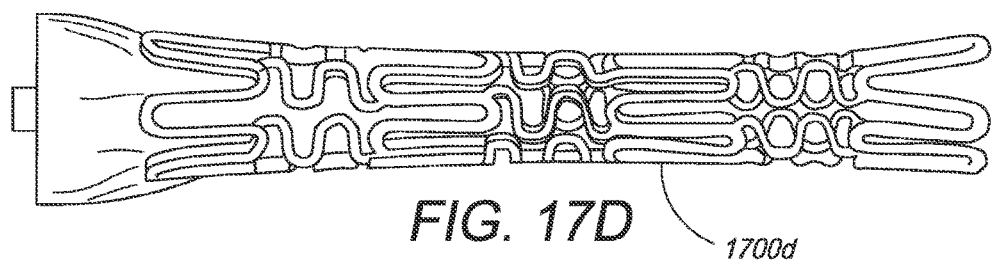
FIG. 17D is an illustration of one embodiment depicting a fifth exemplary configuration of the wire mesh structure.
Figure 17E:
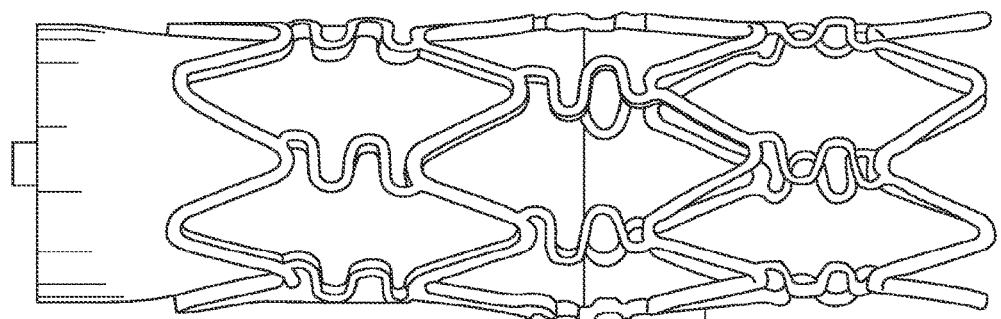
FIG. 17E is an illustration of one embodiment depicting the expanded configuration of the wire mesh structure of FIG. 17D.
Figure 17F:
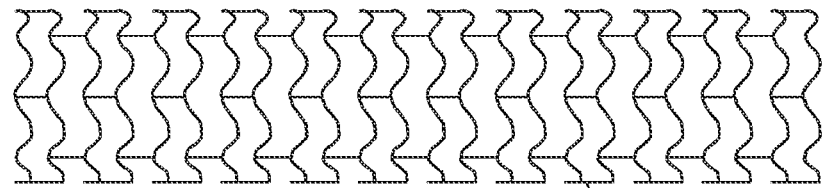
FIG. 17F is an illustration of one embodiment depicting a sixth exemplary configuration of the wire mesh structure.
Figure 17G:
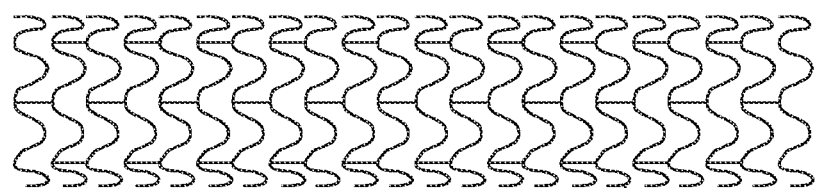
FIG. 17G is an illustration of one embodiment depicting a seventh exemplary configuration of the wire mesh structure.
Figure 17H:
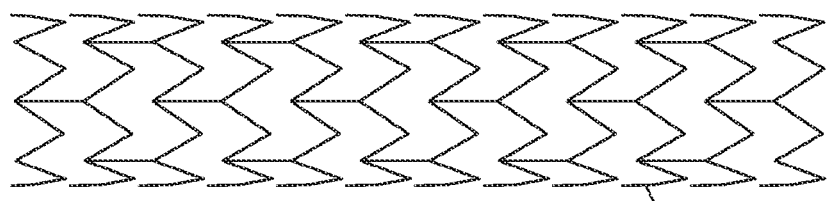
FIG. 17H is an illustration of one embodiment depicting an eighth exemplary configuration of the wire mesh structure.
Figure 17I:
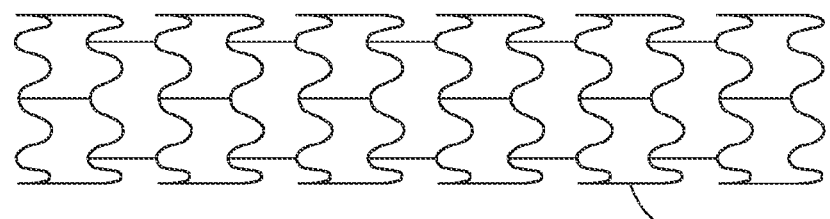
FIG. 17I is an illustration of one embodiment depicting a ninth exemplary configuration of the wire mesh structure.
Figure 17J:
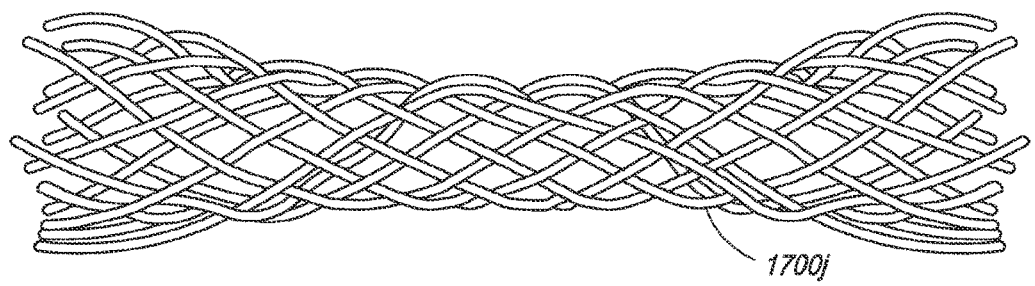
FIG. 17J is an illustration of one embodiment depicting a tenth exemplary configuration of the wire mesh structure; and, FIG. 17K is an illustration of one embodiment depicting an eleventh exemplary configuration of the wire mesh structure.
Figure 17K:
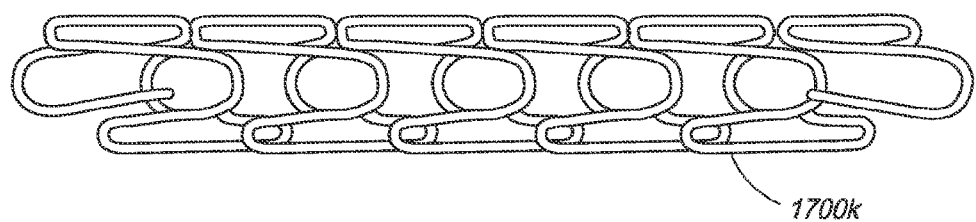

FIGS. 17 through 17K depict various exemplary configurations of the wire mesh structure, 1700, 1700a, 1700b, 1700c, 1700d, 1700e, 1700f, 1700g, 1700h, and 1700i, 1700j, and 1700k, comprised within the intragastric device. As shown in the Figures, the mesh structure can have a plurality of different configurations, with varying degrees of density between the wires components and varying sizes of holes defining the mesh structure. The spatial density may be defined in a plurality of dimensions, including along lengths and spaces a, b, c, d, e, f, g, h, i, j, and k.

It should be appreciated that the present disclosure is intended to provide a teaching of several exemplary embodiments of the present invention and is should not be limited to the specific structures disclosed herein. Other variations of the disclosed embodiments, which would be understood by those of ordinary skill, are covered by the present application and are within the scope of the invention, as further defined by the claims.

The invention claimed is:

1. A stomach occupying device comprising:
   a porous mesh structure configured to reside in a stomach and having a pre-deployment shape with a first volume and a post-deployment shape with a second volume, wherein said first volume is less than said second volume, said porous mesh structure further comprising (1) an upper portion having a plurality of first openings, (2) a middle portion having a second plurality of openings, and (3) a lower portion having a plurality of third openings, and wherein in said post-deployment state said porous mesh structure has a spherical or ovular shape; and
   a sleeve having a length, an enclosed body along said length, an open top end, and an open bottom end, wherein said top end of said sleeve is physically attached to said lower portion;
   wherein said second plurality of openings are larger than either of said first plurality of openings and said third plurality of openings, and
   wherein the second plurality of openings have valves configured to direct ingested food into the porous mesh structure, and the first and third plurality of openings are configured to direct the ingested food out of the porous mesh structure.

2. The stomach occupying device of claim 1 wherein said porous mesh structure comprises a wire mesh structure.

3. The stomach occupying device of claim 1, wherein said porous mesh structure is attached to a catheter, and
   wherein said catheter is configured to induce a change from the pre-deployment shape to said post-deployment shape.

4. The stomach occupying device of claim 1, wherein the upper portion weighs less than the lower portion.

5. The stomach occupying device of claim 1, wherein each of said plurality of first openings is defined by an area where a sum of the areas of the plurality of first openings is equal to a first area, and
   wherein said each of said plurality of third openings is defined by an area where the sum of the areas of the plurality of the third openings is equal to a second area.

6. The stomach occupying device of claim 5, wherein said first area is equal to or larger than said second area.

7. The stomach occupying device of claim 1, wherein said sleeve comprises latex, parylene, polyurethane, polytetrafluoroethylene, fluorinated ethylene-propylene, polyethylene terephthalate and combinations thereof.

8. The stomach occupying device of claim 1, wherein said porous mesh structure further comprises a plurality of vertical elements and a plurality of horizontal elements, wherein said at least one of said plurality of vertical elements and said plurality of horizontal elements comprise a shape memory metal or a shape memory polymer.

9. The stomach occupying device of claim 1, wherein said plurality of said third openings in said lower portion are smaller than said plurality of first openings in said upper portion.

* * * * *

UNITED STATES PATENT AND TRADEMARK OFFICE
CERTIFICATE OF CORRECTION

| | | |
|---|---|---|
| PATENT NO. | : 10,413,436 B2 | |
| APPLICATION NO. | : 14/096505 | |
| DATED | : September 17, 2019 | |
| INVENTOR(S) | : Virender K. Sharma | |

It is certified that error appears in the above-identified patent and that said Letters Patent is hereby corrected as shown below:

On the Title Page

In item (73), the Assignee, change "W. L. Gore & Associates, Inc., Newark, DE (US)" to --SynerZ Medical, Inc., Newark, DE (US)--

Signed and Sealed this
Fifth Day of July, 2022

Katherine Kelly Vidal
*Director of the United States Patent and Trademark Office*